US011000622B2

(12) United States Patent
Krosney

(10) Patent No.: US 11,000,622 B2
(45) Date of Patent: May 11, 2021

(54) UV STERILIZATION APPARATUS, SYSTEM, AND METHOD FOR FORCED-AIR PATIENT HEATING SYSTEMS

(71) Applicant: Mark D. Krosney, Jensen Beach, FL (US)

(72) Inventor: Mark D. Krosney, Jensen Beach, FL (US)

(73) Assignee: Aeroclean Technologies, LLC, Dover, DE (US)

( * ) Notice: Subject to any disclaimer, the term of this patent is extended or adjusted under 35 U.S.C. 154(b) by 371 days.

(21) Appl. No.: 15/693,889

(22) Filed: Sep. 1, 2017

(65) Prior Publication Data
US 2018/0021471 A1 Jan. 25, 2018

Related U.S. Application Data

(60) Continuation-in-part of application No. 14/921,638, filed on Oct. 23, 2015, now abandoned, which is a continuation-in-part of application No. 14/527,449, filed on Oct. 29, 2014, now Pat. No. 9,480,768, which
(Continued)

(51) Int. Cl.
*A61L 9/20* (2006.01)
*A61F 7/00* (2006.01)
*B01D 53/00* (2006.01)

(52) U.S. Cl.
CPC .............. *A61L 9/20* (2013.01); *A61F 7/0085* (2013.01); *A61F 7/0097* (2013.01); *B01D 53/007* (2013.01); *A61F 2007/006* (2013.01); *A61L 2209/111* (2013.01); *A61L 2209/14* (2013.01); *A61L 2209/16* (2013.01); *B01D 2257/91* (2013.01); *B01D 2259/804* (2013.01)

(58) Field of Classification Search
CPC ........ A61L 9/20; A61F 7/0085; A61F 7/0097; B01D 53/007
See application file for complete search history.

(56) References Cited

U.S. PATENT DOCUMENTS

| 5,225,167 A | 7/1993 | Wetzel |
| 5,505,904 A | 4/1996 | Haidinger et al. |
| 5,626,820 A | 5/1997 | Kinkead et al. |
| (Continued) | | |

FOREIGN PATENT DOCUMENTS

| CN | 101639267 A | 2/2010 |
| EP | 2554583 A1 | 2/2013 |
| (Continued) | | |

OTHER PUBLICATIONS

International Preliminary Report on Patentability received from the Korean Intellectual Property Office in International Application No. PCT/US2016/057932 dated Feb. 1, 2018.
(Continued)

*Primary Examiner* — Kevin Joyner
(74) *Attorney, Agent, or Firm* — The Marbury Law Group, PLLC

(57) ABSTRACT

An improvement to UV sterilization and disinfection devices and methods is disclosed. An apparatus for sterilization and disinfection includes: a compact, highly effective air sterilization and disinfection apparatus, which delivers clean, pure air directly into a blower/warmer device for clean and effective management of patient body temperature.

12 Claims, 16 Drawing Sheets

Related U.S. Application Data is a division of application No. 13/951,598, filed on Jul. 26, 2013, now Pat. No. 8,900,519.

(60) Provisional application No. 61/676,407, filed on Jul. 27, 2012, provisional application No. 62/552,547, filed on Aug. 31, 2017.

(56) References Cited

U.S. PATENT DOCUMENTS

| | | | |
|---|---|---|---|
| 5,689,364 | A | 11/1997 | McGregor et al. |
| 5,761,908 | A | 6/1998 | Oas et al. |
| 5,964,792 | A | 10/1999 | Augustine |
| 6,039,926 | A | 3/2000 | Goldman |
| 6,053,968 | A | 4/2000 | Miller |
| 6,254,337 | B1 | 7/2001 | Arnold |
| 6,322,614 | B1 | 11/2001 | Tillmans |
| 6,464,760 | B1 | 10/2002 | Sham et al. |
| 6,641,777 | B1 | 4/2003 | Lombardo et al. |
| 6,797,044 | B2 | 9/2004 | Ou Yang et al. |
| 6,893,610 | B1 | 5/2005 | Barnes |
| 6,949,223 | B2 * | 9/2005 | McEllen ............... A61L 9/015 250/435 |
| 7,175,814 | B2 | 2/2007 | Dionisio |
| 7,498,004 | B2 | 3/2009 | Saccomanno |
| 2005/0163648 | A1 | 7/2005 | Liang |
| 2005/0173352 | A1 | 8/2005 | Burrows et al. |
| 2005/0242013 | A1 | 11/2005 | Hunter et al. |
| 2006/0159594 | A1 | 7/2006 | Parker et al. |
| 2007/0196235 | A1 | 8/2007 | Shur et al. |
| 2008/0095661 | A1 | 4/2008 | Kohler |
| 2009/0004047 | A1 | 1/2009 | Hunter et al. |
| 2009/0041632 | A1 | 2/2009 | Day et al. |
| 2009/0084734 | A1 | 4/2009 | Yencho |
| 2009/0098014 | A1 | 4/2009 | Longstaff |
| 2009/0252646 | A1 * | 10/2009 | Holden ............... A47B 25/00 422/24 |
| 2010/0132715 | A1 | 6/2010 | Litz |
| 2010/0143205 | A1 | 6/2010 | Engelhard |
| 2010/0260644 | A1 | 10/2010 | Day et al. |
| 2011/0033346 | A1 | 2/2011 | Bohlen et al. |
| 2012/0118150 | A1 | 5/2012 | Brizes et al. |
| 2012/0168641 | A1 | 7/2012 | Lizotte |
| 2012/0273340 | A1 | 11/2012 | Felix |
| 2012/0285459 | A1 | 11/2012 | Sata et al. |
| 2013/0238042 | A1 | 9/2013 | Gildersleeve et al. |
| 2013/0313104 | A1 | 11/2013 | Yates et al. |
| 2014/0017135 | A1 | 1/2014 | Boodaghians et al. |
| 2014/0030144 | A1 | 1/2014 | Krosney et al. |
| 2014/0271374 | A1 | 9/2014 | Giles et al. |
| 2014/0348701 | A1 | 11/2014 | Kirschman |
| 2016/0038624 | A1 * | 2/2016 | Krosney ............. B01D 53/007 422/121 |

FOREIGN PATENT DOCUMENTS

| | | |
|---|---|---|
| EP | 2 921 183 A1 | 9/2015 |
| JP | 2012-512723 A | 0/2012 |
| JP | 2000-008178 A | 1/2000 |
| JP | 2000-070928 A | 3/2000 |
| JP | 2001-224672 A | 8/2001 |
| JP | 2005-166180 A | 6/2005 |
| JP | 2005-203437 A | 7/2005 |
| JP | 2005-253799 A | 9/2005 |
| JP | 2007-511279 A | 5/2007 |
| JP | 2008-259809 A | 10/2008 |
| JP | 2009-22903 A | 2/2009 |
| JP | 2009-532200 A | 9/2009 |
| JP | 2011-530542 A | 12/2011 |
| WO | 2005/011753 A1 | 2/2005 |
| WO | 2007113537 A1 | 10/2007 |
| WO | 2010/071814 A1 | 6/2010 |
| WO | 2011/087100 A1 | 7/2011 |
| WO | 2015/131243 A1 | 9/2015 |
| WO | 2017/070359 A1 | 4/2017 |

OTHER PUBLICATIONS

International Search Report and Written Opinion of the International Searching Authority for International Application No. PCT/US2018/024229 dated Jul. 13, 2019. 12 pages.

International Search Report and the Written Opinion of the International Searching Authority received from the Korean Intellectual Property Office in PCT Application No. PCT/US2018/024229 dated Jul. 13, 2018.

1st Examination Report received from the Saudi Patent Office in Saudi Arabia Patent Application No. 516370810 dated Nov. 13, 2017.

Extended European Search Report from the European Patent Office in Application No. 14529503.4-1370 / 3024503 in International Application No. PCT/US2014/048144 dated Feb. 2, 2017.

International Search Report and the Written Opinion of the International Searching Authority in International Application No. PCT/US2016/057932 dated Feb. 3, 2017.

Extended European Search Report received from the The Hague Patent Office in related European Application No. EP 16 85 8222 dated May 22, 2019 PCT/US2016/057932.

European Communication Pursuant to Rules 70(2) and 70a(2) EPC from the European Patent Office in related European Application No. EP 16 85 8222 dated Jun. 7, 2019 PCT/US2016/057932.

First Notification of Reasons for Refusal received from the Japanese Patent Office in related Japansese Patent Application No. 2016-530064 dated May 31, 2018.

International Preliminary Report on Patentability received from the Korean Intellectual Property Office in related International Application No. PCT/US2018/024229 dated Dec. 19, 2019.

First Examination Report (FER) received from the Indian Patent Office in related Indian Patent Application No. 201637004406 dated Oct. 25, 2020.

Notification of Reasons for Refusal in related Japanese Patent Application No. 2018-540690 dated Sep. 3, 2020.

Written Opinion of the International Preliminary Examination Authority in related PCT Application No. PCT/US2018/024229 dated Oct. 24, 2019.

1st Office Action received from the European Patent Office in related European Patent Application No. 14 829 593.4-1104 dated Nov. 6, 2020.

International Search Report and the Written Opinion of the International Searching Authority received from the Korean Intellectual Property Office in related International Application No. PCT/US2018/024228 dated Jul. 13, 2018.

International Preliminary Report on Patentability received from the Korean Intellectual Property Office in related International Application No. PCT/US2018/024228 dated Dec. 16, 2019.

* cited by examiner

UV STERILIZATION APPARATUS, SYSTEM, AND METHOD FOR FORCED-AIR PATIENT HEATING SYSTEMS

RELATED APPLICATIONS

This application is a continuation-in-part of U.S. patent application Ser. No. 14/921,638, filed Oct. 23, 2015, which is a continuation-in-part of U.S. patent application Ser. No. 14/527,449 filed Oct. 29, 2014, now U.S. Pat. No. 9,480,768 which is a divisional of U.S. patent application Ser. No. 13/951,598 filed Jul. 26, 2013, now U.S. Pat. No. 8,900,519 which claims the benefit of priority to U.S. Provisional Patent Application No. 61/676,407, filed Jul. 27, 2012.

Each of the foregoing applications, collectively referred to herein as "the priority documents," is incorporated herein by reference in its entirety.

FIELD OF THE INVENTION

This invention relates generally to air sterilization and disinfection, and more particularly to an apparatus, system, and related method for sterilizing and disinfecting air in forced-air patient heating systems.

BACKGROUND

According to the Centers for Disease Control, there are over 51 million surgeries performed in the United States alone each year (Centers for Disease Control and Prevention Online FASTSTATS—Inpatient Surgery). The majority of these surgeries require advanced techniques for regulating the patient's core body temperature. It is known in the art that a typical operating room is kept at about 20° C., thereby making it difficult to keep a patient's core body temperature between the desired 36-38° C. range. To further complicate matters, general anesthesia accelerates temperature loss from a patient. Without supplemental warming in this environment, a patient's core body temperature would quickly drop below 35° C. to a hypothermic state. Persons having ordinary skill in the art will appreciate that this may lead to serious complications such as increased incidents of blood clots, wound infection, and cardiac arrest. For these reasons, it is important to maintain a patient's normal body temperature during surgery. It is well known in the art to utilize a warming device in order to maintain the patient's normal body temperature.

There are multiple devices known in the art that are used to warm a patient in an operating room during and after a surgical procedure. Common methods of patient warming include passive warming, such as through the use of insulators, and active heating, through the use of convection or conduction based devices. One of the most common warming methods is known in the art as forced-air convection (Mahoney C B, and Odom, J. "Maintaining intraoperative normothermia: a meta-analysis of outcomes with costs"). Forced-air convection systems are well-described in the prior art and typically use a pump and heater system to blow warm air through a flexible hose and into an inflatable blanket, gown, or other covering in contact with the patient. The covering is typically inflated by the introduction of the forced-air through an inlet. An aperture array on the underside (patient-side) of the covering exhausts the heated air directly to the patient's body, thereby creating an ambient environment around the patient, the characteristics of which are determined by the temperature of the thermally-controlled forced air, which has the effect of raising the patient's body temperature through this forced-air convection.

While the prior-art forced-air convection warming systems have achieved their objective of regulating patient temperature, they have also brought with them serious, and undesirable, side-effects.

Studies, such as those reported in "Convection warmers— not just hot air," by Avidan, Jones, Ing, Khoosal, Lundgren, and Morrell, have indicated that forced-air convection warming systems are a potential source for nosocomial infection. Nosocomial infections are infections that have been caught in a hospital and are potentially caused by organisms that are resistant to antibiotics. A nosocomial infection is specifically one that was not present or incubating prior to the patient's being admitted to the hospital, but occurring within 72 hours after admittance to the hospital.

Other studies such as those reported by Albrecht, Gauthier, and Leaper, in "Forced-air warming a source of airborne contamination in the operating room?" found that forced-air warming systems have the potential to generate and mobilize airborne contamination in the operating room. The design of forced-air warming blowers was found to be questionable for preventing the build-up of internal contamination and the emission of airborne contamination into the operating room. A significant percentage of forced-air warming blowers with positive microbial cultures were emitting internally generated airborne contamination within the size range of free floating bacteria and fungi (<4 urn) that could, conceivably, settle onto the surgical site.

Although forced air warming systems are the preferred method of patient warming, the design of the current state of the art warmers have inherent design flaws that contribute directly to the delivery of airborne pathogens to the patient. Current air warmers are small. Their compact size is intentional in order to not be obtrusive in the operating suite, as well as portable to go with the patient from room to room. These small units are more often than not hung off the side or foot of the patient bed. This location places the air intake of the unit closer to the floor, and most importantly, outside of the sterile field.

Pathogen laden air is drawn in to the unit, where it then passes over a heating element, and is then expelled through a hose to the patient location, typically through the use of a blanket or covering, as described above. While most of these units incorporate a particulate filter, these filters do not keep out most pathogens, and their effectiveness depends directly on the care and maintenance of the unit. Like all particulate filters, they need to be regularly cleaned and/or replaced.

Once the pathogens have entered the unit, the heating chamber creates a breeding ground for fungi and other pathogens that thrive in warm, dark environments.

All of this combines to create a direct path for pathogen-laden air to be introduced directly into the sterile field—and directly to the patient.

There is a growing demand for improvements in hospital settings to reduce the transmission of pathogens. This demand is driven by hospitals that have to deal with an increasing amount of cases of infections, not caused by the patient's diagnosis upon admission, but rather, due to airborne pathogens that exist in a hospital environment. Highly effective devices and methods of removing airborne pathogens using UV LEDs are disclosed in U.S. Pat. No. 8,900,519, as well as the other priority documents, incorporated by reference as if fully set forth herein.

It would, therefore, be desirable and beneficial to have an apparatus, and related system and method that purifies and sterilizes air before warming the air and distributing the heated air to the patient. Furthermore, it would be desirable to have an air sterilization and purification device that is compact, quiet, and unobtrusive, while also being highly effective in the removal and/or neutralization of harmful airborne pathogens in a forced-air warming system for patient temperature control.

The present invention is unique when compared with other known devices and methods because the present invention provides: (1) a compact footprint; (2) effective pathogen removal directly at the site of the blower/warmer; and (3) ease of maintenance.

The present invention is unique in that it is structurally different from other known devices or solutions. More specifically, the present invention is unique due to the presence of: (1) an airflow and irradiation management chamber comprising a single or a plurality of turbulators; (2) UV LEDs embedded in the walls of the airflow and irradiation management chamber; (3) one or more high efficiency particulate filters and/or HEPA filters; and (4) a blower/warmer that heats and delivers thermally controlled air that has been sterilized and, effectively, pathogen-free.

SUMMARY OF THE INVENTION

The present invention discloses an improvement to the UV sterilization and disinfection devices and methods disclosed in the priority documents, and relates to an apparatus, a system, and a method associated with the apparatus and system. With respect to the apparatus, embodiments include a compact, highly effective air sterilization and disinfection apparatus, which delivers clean, pure air directly into a blower/warmer module for clean and effective management of patient body temperature.

In a preferred embodiment, the apparatus combines wavelength-specific, high-output UV LEDs with an airflow and irradiation management chamber that facilitates the necessary UV dosage by increasing the dwell time of the airflow being treated. This apparatus can be used in hospitals, clinics, operating rooms, and other environments where it is desired to deliver clean, pure air directly into a blower/warmer module for clean and effective management of patient body temperature. The compact, quiet, and unobtrusive nature of this apparatus makes it particularly well suited for use in surgical environments.

Generally, the apparatus comprises an electronics and control module, a means of drawing room air into, and expelling from, the apparatus, a heater, an air management chamber, an array of wavelength-specific, high-output UV LEDs, a particulate filter means, and a housing.

With respect to the particulate filter means, said filter may be chosen from various materials known in the art to filter airborne particles such as high efficiency particulate filters and HEPA filters.

With respect to the apparatus it should be further noted that the selection of the wavelength of the UV LEDs as well as the design of the airflow and irradiation management chamber is critical in order to manage the level and duration of UV light dosage in order to effectively sanitize the incoming air.

Generally, the steps to carry out the method associated with the apparatus are comprised of: drawing air into the apparatus; exposing the air to sufficient UV radiation to achieve at least a 2 log (99%) kill rate; heating the now sterilized air; and expelling the now heated and sterilized air to the patient, whereby the apparatus is used to deliver clean, pure air to the patient for clean and effective management of patient body temperature.

BRIEF DESCRIPTION OF THE DRAWINGS

These and other features, aspects, and advantages of the present invention will become better understood with regard to the following description, appended claims, and accompanying drawings where:

DETAILED DESCRIPTION OF THE DRAWINGS

Figure 1:
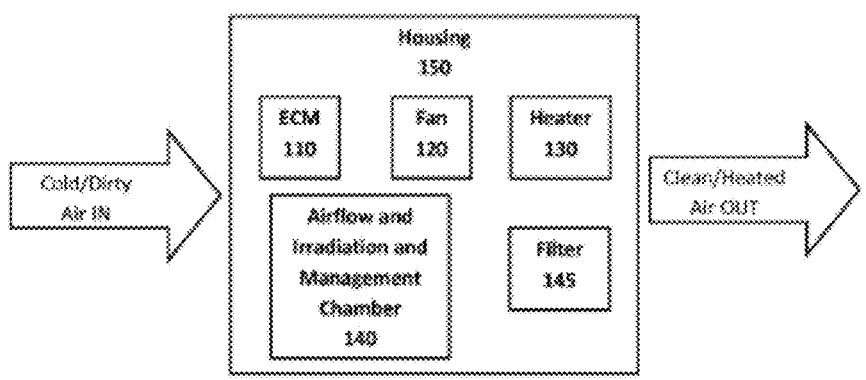
FIG. 1 shows a simplified block diagram representation of an embodiment of the invention, as shown.

In the Summary of the Invention above and in the Detailed Description of the Drawings, and the claims below, and in the accompanying drawings, reference is made to particular features (including method steps) of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with and/or in the context of other particular aspects and embodiments of the invention, and in the invention generally.

The term "UV radiation" is used herein to mean high energy UV-C photons with wavelengths shorter than 290 nm, which are capable of traversing cellular walls. In various embodiments, the UV radiation utilized for air treatment may be at one or multiple wavelengths within the range of 200 to 320 nm range.

The terms "flux" and "radiation flux" are used herein to mean the amount of radiation at the specified wavelength that reaches the surface of airborne pathogens. The terms "dwell time" and "residence time" are used herein to refer to the duration of time that the airborne pathogens remain exposed to the radiation flux.

The terms "contaminants" is used herein to refer to impurities, including all of biological agents (e.g., pathogens), chemical agents, pollutant particles, volatile organic compounds, and chemical vapors.

The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)," this means a range whose lower limit is the first number and whose upper limit is the second number. For example, 25 to 100 mm means a range whose lower limit is 25 mm, and whose upper limit is 100 mm.

While the specification concludes with claims defining the features of embodiments of the invention that are regarded as novel, it is believed that the invention will be better understood from a consideration of the following description in conjunction with the figures, in which like reference numerals are carried forward.

The Apparatus

One embodiment, in the form of a convective air warming, sterilization and disinfection apparatus 100, as shown generally in the figures and particularly in FIG. 1, can comprise: an electronics and control module 110; a fan 120; a heater 130; an airflow and irradiation and management chamber 140; a filter 145; and a housing 150 whereby the apparatus is capable of achieving at least a 2 LOG kill of airborne pathogens, warming the sterilized air, and delivering it to the patient.

This apparatus can be used in hospitals, clinics, operating rooms, and other environments where it is desired to deliver clean, pure air directly into a blower/warmer module for clean and effective management of patient body temperature. The compact, quiet, and unobtrusive nature of the disclosed embodiments makes them particularly well suited for use in surgical environments.

For simplicity of disclosure, certain components of the apparatus are described here in general terms as the specifics of the component would be known to one having ordinary skill in the art. For example, the electronics and control module 110 may comprise various sub-components and features as would be necessary to provide and regulate power to the various parts of the apparatus, receive input from a user, and provide feedback to a user. The fan 120 may be chosen among any of the various means of producing an airflow as is known in the art. Similarly, the heater 130 may be chosen among any of the various means of heating air as is known in the art. The filter 145 is a high efficiency particulate filtration means as is known in the art, for example, a high-efficiency particulate air (HEPA) filter. In some embodiments, the HEPA filter may have a minimum efficiency of 99.97% arrestance at 0.3 micrometers, as set forth by standards of the U.S. Department of Energy.

Figure 2:
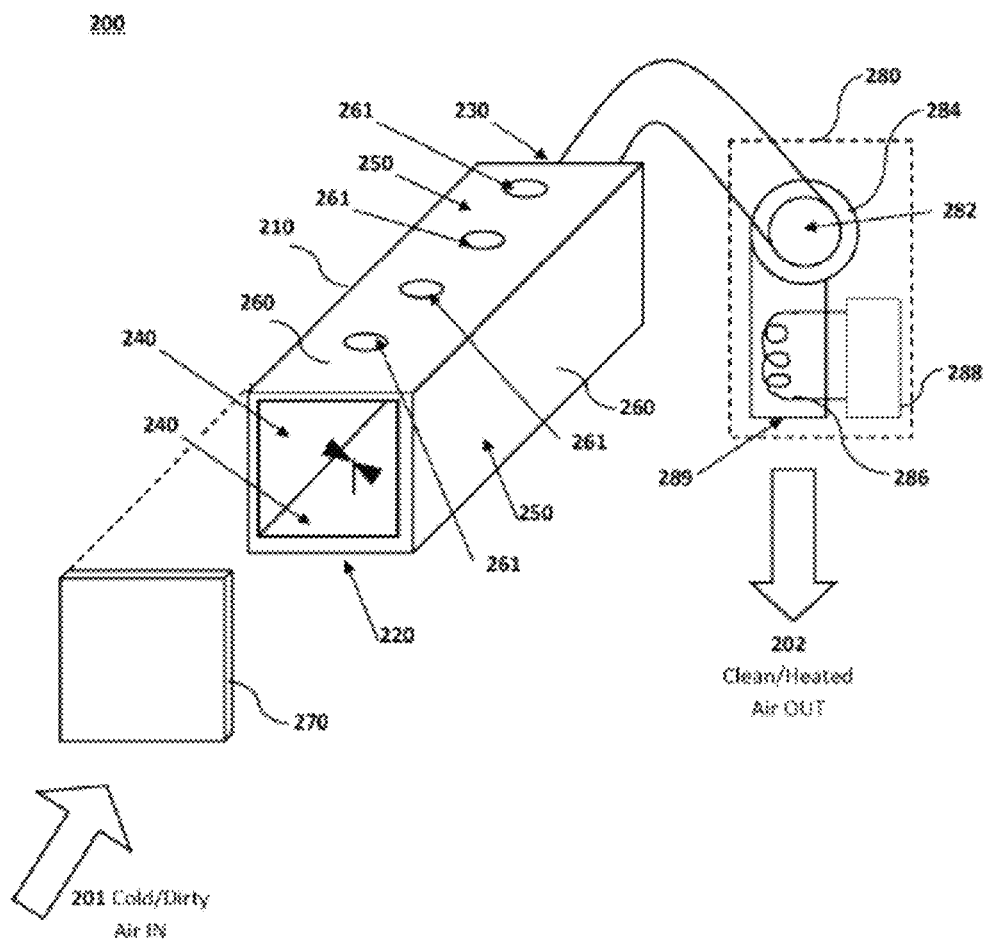
FIG. 2 shows a perspective view of an embodiment of the invention, as shown.

Referring now to the figures in general and FIG. 2 in particular, another embodiment of the present invention discloses an apparatus for delivering pathogen-reduced air in a forced-air patient heating system 200, the embodiment apparatus comprising: an airflow and irradiation management chamber 210 that creates a turbulent flow such that airborne pathogens are exposed to a dosage of UV radiation sufficient to penetrate and kill the pathogens, comprising: an inlet 220, an outlet 230, an inner surface 240, an outer surface 250, and a wall 260 bounded by the inner surface and the outer surface; a high efficiency particulate filter 270 operatively coupled to the airflow and irradiation management chamber inlet; and a heater/blower assembly 280 comprising: an inlet 282 operatively connected to the airflow and irradiation management chamber outlet 230, a fan 284, a heater 286, an electronics and control module 288, and an outlet 289.

Figure 3:
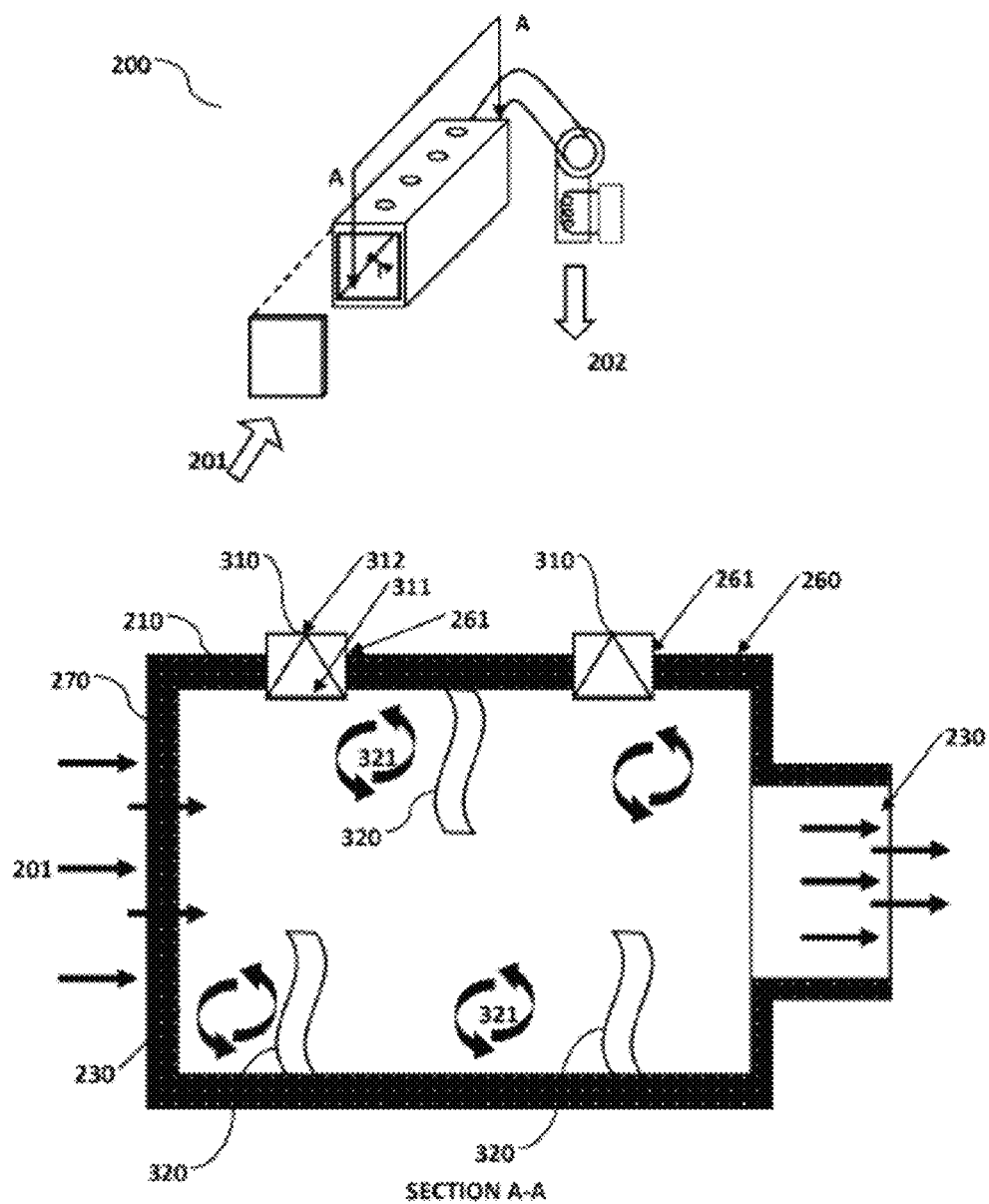
FIG. 3 shows a composite view of an embodiment of the invention, including a cross-sectional view of an embodiment of an airflow and irradiation management chamber, as shown.

Referring now to FIGS. 2 and 3, another embodiment of the present invention discloses an apparatus 200 for delivering forced air to a patient temperature control system by warming, sterilizing, and disinfecting air, the apparatus comprising: an ultra-violet (UV) light blocking structure 210, configured to receive an air flow with a one or more airborne pathogens 201, said UV light blocking structure comprising an inlet 220, an outlet 230, bounding surface 240, 260 between the inlet and the outlet defining an inner area and an outer area, and a one or more aperture 261 through the bounding surface between the inner area and the outer area; a one or more UV light emitting diode (LED) 310 with an emitter portion 311 and a non-emitter portion 312, insertedly related to the one or more aperture such that the emitter portion is oriented toward the inner area of the UV light blocking structure and further inserted with sealing means as is known in the art to ensure that UV light does not escape through the aperture; a one or more turbulator 320 located within said inner area of the UV light blocking structure; a high efficiency particulate filter 270 operatively connected to the inlet 220 of the UV light blocking structure 210; and a heater/blower assembly 280 comprising: an inlet 282 operatively connected to the UV light blocking structure outlet 230; a fan 284; a heater 286; an electronics and control module 288; and an outlet 289 whereby the apparatus expels clean heated air 202.

The turbulators 320 disclosed in this embodiment, and throughout the disclosure, are physical structures designed to create turbulence. More specifically, the turbulators interact with an airflow, converting a laminar flow into a turbulent flow 321. One having ordinary skill in the art would recognize that the turbulators may be chosen from various configurations including, but not limited to, vanes, airfoils, v-gutters and area(s) of sudden expansion.

Figure 4:
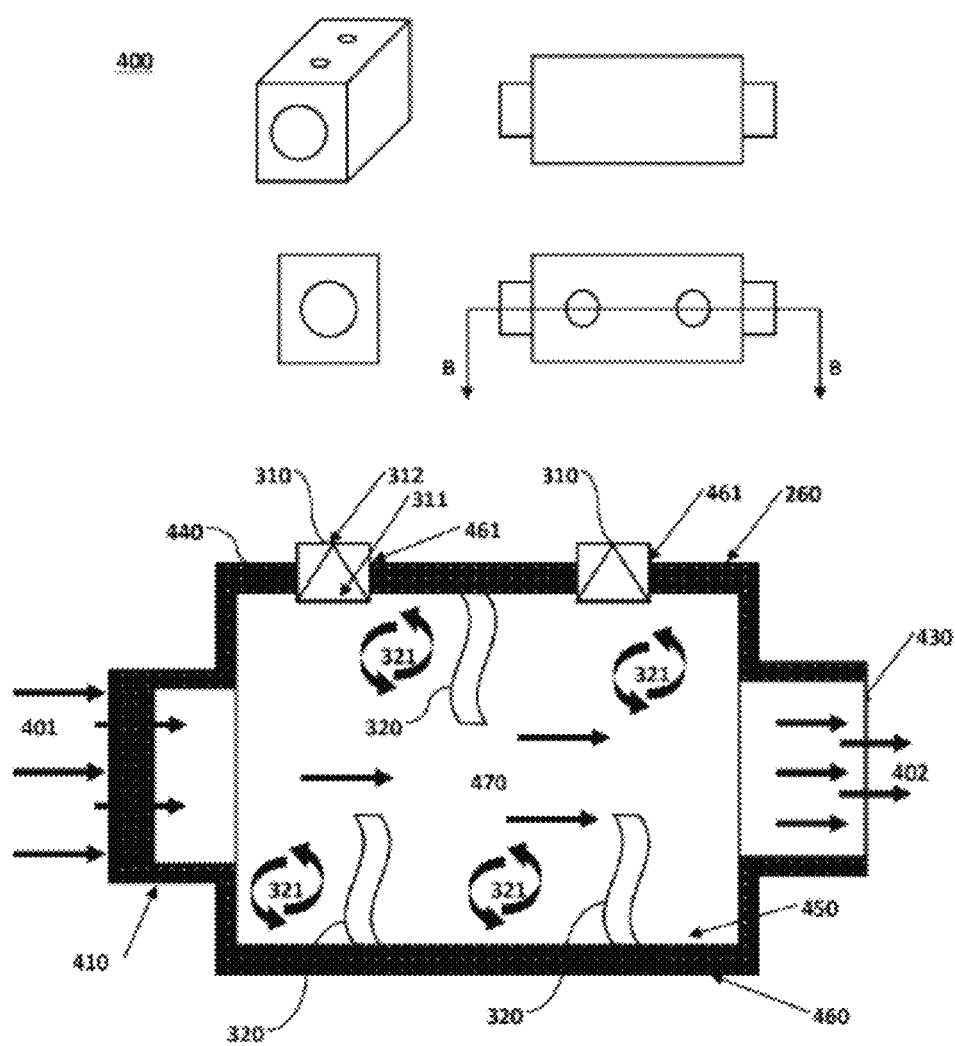
FIG. 4 shows a composite view of an embodiment of the invention, including perspective, orthographic projection, and cross-sectional views of an apparatus for sterilizing and disinfecting air.

We refer now to FIG. 4 where we discuss another embodiment of the present invention disclosing an apparatus 400 for sterilizing and disinfecting air, the apparatus comprising: an inlet portion 410 configured to receive an air flow 401; a high efficiency filter operatively coupled to the inlet portion 410; an outlet portion 430 configured to expel the now sterilized air flow 402; a non-ultraviolet (UV) light transmissive surface portion 440, comprising a UV light reflective inner surface 450, an outer surface 460, a one or more turbulator 320, and a one or more aperture, said non-UV light transmissive surface defining a substantially enclosed area 470 between the inlet portion and the outlet portion through which said air flow passes; and a one or more UV light emitting diode (LED) 310 inserted into said one or more apertures 461 such that a UV radiation is emitted into said enclosed area 470 thereby exposing said air flow to said UV radiation.

Another embodiment of the present invention discloses a kit for retrofitting an existing forced-air convection heater device for providing clean, thermally-controlled air to patients for the prevention of hypothermia as might occur intraoperatively or postoperatively. Embodiments of the kit may comprise: an ultra-violet (UV) light blocking structure, configured to receive an air flow with a one or more airborne pathogens, said UV light blocking structure comprising an inlet, an outlet, a bounding surface between the inlet and the outlet defining an inner area and an outer area, and a one or more aperture through the bounding surface between the inner area and the outer area; a one or more UV light emitting diode (LED) with an emitter portion and a non-emitter portion, insertedly related to the one or more aperture such that the emitter portion is oriented toward the inner area of the UV light blocking structure; a one or more turbulator located within said inner area of the UV light blocking structure; a high efficiency particulate filter located at the inlet of the UV light blocking structure; a hardware kit; and a housing. The hardware kit is configured to contain all necessary mechanical and electrical hardware components required to install the kit onto the existing device. The housing is configured to enclose all of the kit components and further comprises mounting and attachment interfaces so that, once installed, the kit forms a complimentary structure to the existing device.

In some embodiments of the present invention, the lower housing of the existing warmer/blower device is removed and discarded or recycled. The kit embodiment described above would then be installed such that the outlet of the airflow and irradiation management chamber (also described here as the ultraviolet light blocking structure) is sealably coupled to the inlet of the existing device's heater portion, the UV LED's are electrically connected to the electrical supply of the device, and the kit housing is mechanically attached to the existing device's housing using the mechanical and electrical components of the kit's hardware kit.

Another embodiment of the present invention is disclosed herein as an apparatus configured to be attached to, and accept an airflow from, the distal end of a hose, which is attached at the hose's proximal end to an airflow outlet of a convective air warming device. Since there may be situations where it is not desirable, or possible, to retrofit an existing warmer/blower device, UV sterilization of the warmed air prior to reaching the patient may be accomplished by the use of this embodiment of the present invention which comprises: an airflow and irradiation management chamber as described herein with an inlet and an outlet; and a housing.

The apparatus may further comprise a first adaptor means for sealably interfacing the warmer/blower device hose distal end to the airflow and irradiation management chamber's inlet, as well as a second adaptor means for sealably interfacing the airflow management chamber's outlet with the inlet of a patient warming blanket or other covering configured for convective air patient warming. The first and second adaptor means include various mechanical interfaces as will be readily appreciated by one having skill in the art. Male-Female couplings, gaskets, reducers, expanders, and clamps are all examples of adaptors that may be chosen as the first and second adaptor means.

In this embodiment, the UV LEDs of the airflow and irradiation management chamber will need to be powered separately from the warmer/blower device. As such, it is contemplated to be within the scope of this embodiment of the present invention that the apparatus may further comprise a power supply and regulation means. This power supply and regulation means may include, but is not limited to, a power plug, a voltage regulator, a transformer, a circuit breaker, and circuitry for powering, monitoring, and regulating the UV LEDs.

An alternative means of powering the UV LEDs in this embodiment may comprise a rechargeable battery pack. This rechargeable battery pack would be electrically connected to the system in order to provide power to the UV LEDs and any additional circuitry. The battery pack may be recharged by conventional charging means, as is known in the art, or, alternatively, it could be recharged by electricity generated by the rotational motion of turbines placed within the airflow and irradiation management chamber. The airflow current expelled from the Warmer/blower system and passing through the airflow and irradiation management chamber would flow past the vanes of the turbines causing them to rotate. These turbines may be utilized in concert with, or instead of, turbulators as described above, creating a turbulent flow within the airflow and irradiation management chamber, and also generating an electrical current which is fed back to a charging circuit means in order to recharge the batter pack.

It is well known in the art that the warmer/blower device in patient warming systems is located at some distance from the patient. In these cases, the warmed air is delivered to the patient (typically to a blanket or other covering means) via a hose. In embodiments of the present invention where the UV sterilization of the air is accomplished at the distal (patient) end of the hose, that embodiment of the invention may further comprise a hose that replaces the existing device's hose. Said replacement hose would comprise means as is known in the art for interfacing with the existing warmer/blower as well as to the US sterilization device. The replacement hose would further comprise integral conductor means for connecting the UV sterilization device to power source. It would be clear to one having ordinary skill in the art that such integral conductor means would include such components as multiple insulated conductors integrally molded into the wall of the replacement hose with electrical connection means on each end.

It is contemplated to be within the scope of the present invention that seals, gaskets, baffles, and other light blocking means as is known in the art are implemented throughout the invention in order to prevent UV light from escaping the apparatus.

Embodiments of the invention disclosed herein may further comprise safety interlock means so that if any part of the system were to become open, exposing the UV LEDs, then the system would shut off the UV LEDs or the unit entirely so as to protect the user from exposure to UV light, electricity, and/or moving parts. Safety interlock means may include various solutions known in the art including, but not limited to, relays, contact closures, and circuit breakers.

Embodiments of the invention disclosed herein may further comprise a timer means to indicate to a user when it is time to replace the filters. Timer means may include various solutions known in the art including, but not limited to, processors and circuitry configured to notify the user via a visual indicator after a predetermined time of operation has elapsed.

It would be clear to one skilled in the art, as well as within the scope and intention of this disclosure, that while the above embodiment has been described as a UV sterilization apparatus connected to clean the airflow between the warmer/blower hose and the inflatable blanket/covering, it may equivalently be installed in between the warmer/blower device and the warmer/blower hose to the same effect.

It would be clear to one skilled in the art that, while the components of the embodiment are described here in a particular configuration or "order", it is still contemplated to be within the scope of the present invention to configure the components in a different "order" and still achieve the same invention. For example, an embodiment of the present invention may comprise an air flow that first passes through a filter, then through the airflow and irradiation management chamber, then into the heater, then expelled out of the unit through the action of a fan or compressor. Alternatively, the order of those components may be changed such that the airflow first passes through a filter, then through a fan or compressor, then into an airflow and irradiation management chamber, then into a heater, and then out of the unit.

Furthermore, embodiments disclosed and discussed here are intended to encompass the UV sterilization of air in conjunction with a warmer/blower device, where the UV sterilization device sterilizes air prior to entering the warmer/blower, between the warmer/blower and the output hose, or at the end of the output hose.

Furthermore, embodiments may comprise one or more than one of any component. For example, in addition to the embodiment described above, an embodiment may comprise a first filter at the unit inlet, a first fan at the unit inlet, a one or more airflow and irradiation management chambers, a second filter at the outlet of the one or more airflow and irradiation management chambers, a second fan between the one or more airflow and irradiation management chambers and a one or more heaters, a third fan between the one or more heaters and the unit outlet, and a third filter at the unit outlet.

The Airflow and Irradiation Management Chamber (see, generally, 140, 200, and 400).

Building upon the teachings disclosed in the priority documents, which have been incorporated by reference herein, we now discuss an airflow and irradiation management chamber. Commercially, the airflow and irradiation management chamber may be known as a STERITUBE™ or a STERIDUCT™.

Referring to the figures in general, and to FIG. 4 in particular, the airflow and irradiation management chamber 400 is comprised of a hollow cross sectional area which is extruded to a desired length such as to define an inner surface 450, an outer surface 460 an inlet 410 and an outlet 430.

An embodiment of the airflow and irradiation management chamber may comprise a cross-sectional area that is substantially consistent throughout the length of the airflow and irradiation management chamber.

A further embodiment of the airflow and irradiation management chamber may comprise a cross-sectional area that varies in shape and/or size throughout the length of the airflow and irradiation management chamber.

The cross section of the one or more airflow and irradiation management chamber may be circular, elliptical, rectangular, or any other shape as may be chosen to maximize the airflow through the desired package size. Each airflow and irradiation management chamber is designed to sustain a specific volumetric throughput.

Embodiments of the airflow and irradiation management chamber may be substantially straight, substantially curved, or comprised of a combination of substantially straight and curved sections.

The airflow and irradiation management chamber itself may be manufactured utilizing various methods and materials as may be known in the art including, but not limited to, extruded plastics, formed metals, or a combination of materials.

Embodiments of the airflow and irradiation management chamber may further comprise a surface treatment on the inner surface 450 that provides for a diffuse reflection of the UV light. The use of diffuse reflectors increases the efficiency of the UV irradiation field by scattering the UV light rays, as opposed to specular reflective surfaces (such as polished metals) that merely reflect the UV ray at an angle equal to the angle at which the ray hits the surface. This diffuse reflection may be accomplished through a microtexture, a coating, or a laminated material, such as polytetrafluoroethylene (PTFE).

Embodiments of the airflow and irradiation management chamber further comprise a one or more turbulators 320 located within the hollow section of the airflow and irradiation management chamber. Turbulators disrupt the airflow, by changing laminar airflow 401 into a turbulent airflow 321, thus ensuring that the airborne pathogens remain exposed to UV radiation for a sufficient amount of time such that the radiation can kill the pathogen. Turbulators may be chosen from various forms known in the art, including, but not limited to, sudden expansion, turbine vanes, airfoils, v-gutters, grooves, ridges, and baffles.

The wall of the airflow and irradiation management chamber 260, that area bounded by the inner surface 450 and the outer surface 460, comprises a material and/or surface finish, that blocks UV light from passing through the wall. The airflow and irradiation management chamber is not, as may otherwise be known in the art, a "light pipe", "light conduit", or other means of transmitting UV light through any means of internal reflection or refraction. Embodiments of the airflow and irradiation management chamber comprise one or more apertures 461 creating openings in the airflow and irradiation management chamber wall configured to accept one or more UV LEDs. As discussed above, each UV LED is sealed, using a sealing means as is known in the art, to the aperture so that no UV light may escape.

The UV LEDs 312

The efficacy of UV light, especially in the "germicidal" spectrum, for the killing of pathogens is well known in the art. UV LEDs, specifically, are well-disclosed in the priority documents and, for brevity, will not be further discussed here. UV LEDs are chosen for this apparatus because of their size, power, and long life. The UV LEDs are selected based upon the desired wavelength and power rating. The number and distribution of these UV LEDs in the airflow and irradiation management chamber are to be such as to maximize the radiant flux within each airflow and irradiation management chamber.

Embodiments of the present invention comprise a one or more UV LEDs sealably assembled into the one or more apertures in the airflow and irradiation management chamber wall such that the one or more UV LEDs emit UV light into the interior of the airflow and irradiation management chamber, namely, that area defined and enclosed by the inner surface of the airflow and irradiation management chamber through where the pathogen laden airflow passes between the airflow and irradiation management chamber inlet and the airflow and irradiation management chamber outlet. The one or more UV LEDs are electrically connected to the electronics and control module.

The Heater (See, Generally, 130 and 286)

Embodiments of the present invention may further comprise a means for heating the airflow. This heating means may be accomplished by any of various methods known in the art, for example, by introducing a current to a length of wire with a resistance high enough to generate heat as the current passes through it the heating means is electrically connected to the electronics and control module and configured so as to be in the path of the airflow such that, as the airflow comes in contact with the heater means, heat energy is transferred to the airflow, thereby warming the air.

The Fan (See, Generally, 120 and 284)

Embodiments of the present invention further comprise a means for creating an airflow through the unit. Specifically, the airflow is defined as the flow of air entering the unit through the unit inlet and exiting the unit through the unit outlet Embodiments may have one or more than one inlet and one or more than one outlet.

Preferred embodiments of the means for creating an airflow through the unit comprise a fan that is capable of producing an airflow through the various components of the unit and that is electrically connected to the electronics and control module.

The Electronics and Control Module (See, Generally, 110 and 288)

Embodiments of the present invention comprise an electronics and control module. The various electrical components, such as UV LED's, heater, and fan, are electrically connected to the electronics and control module. The electronics and control module may further comprise one or more of the following, as may be known in the art: power input means; power regulation means; processing means; display means; user input means; temperature sensing and reporting means; timer means; and UV radiation sensing and reporting means.

The Housing 150

Embodiments of the present invention further comprise a housing. The housing encloses and locates the other components and protects the user from exposure to the internal components and has a one or more inlet opening coupled to the one or more input to the one or more airflow and irradiation management chambers and a one or more outlet opening coupled to the one or more airflow output from the unit.

The Hardware Kit

Embodiments of the present invention may further comprise a hardware kit (not shown]. The hardware kit may further comprise mechanical and electrical components. The mechanical components may include, but are not limited to, screws, nuts, bolts, washers, seals, gaskets, caps, and connectors. The electrical components may include, but are not limited to, cables, wire harnesses, electrical connectors, switches, wirenuts, circuit boards, circuit breakers, and fuses.

The System

Embodiments of the present invention may comprise a system for providing clean, thermally-controlled air to patients for the prevention of hypothermia as might occur intraoperatively or postoperatively. Embodiments of the system may comprise: a particulate filter apparatus; a UV LED air sterilization apparatus capable of achieving at least a 2 LOG kill of airborne pathogens; a heater apparatus; a blower apparatus; an electronics and control apparatus; a flexible hose apparatus; and an inflatable thermal patient covering apparatus.

The Method

Embodiments of the present invention include method steps integral to the use and operation of the disclosed apparatus and system. Embodiments of the related method for providing clean, thermally-controlled air to patients for the prevention of hypothermia as might occur intraoperatively or postoperatively, may comprise the steps of: providing a patient temperature control system comprising; a high performance particulate filter or HEPA filter apparatus; a UV LED air sterilization apparatus capable of achieving at least 2 LOG kill of airborne pathogens; a heater apparatus; a blower apparatus; an electronics and control Apparatus; a flexible hose apparatus; and an inflatable thermal patient covering apparatus; then drawing an ambient air flow through the particulate filter apparatus; exposing the ambient air flow to a UV radiation within the UV LED air sterilization apparatus; heating the ambient air flow with the heater apparatus; forcing the ambient air flow, now heated and sterilized, through the flexible hose apparatus; inflating the thermal patient covering apparatus with the now heated and sterilized ambient air flow; and expelling the now heated and sterilized ambient air flow from the inflatable patient covering apparatus to the patient, whereby the apparatus is used to deliver clean, pure air to the patient for clean and effective management of patient body temperature.

Other embodiments provide an effective, safe, and convenient methods for substantially eliminating airborne pathogens by retrofitting a sanitizing chamber within an existing warming blanket system to create an air treatment system for the warming blanket. The air treatment system may be compact and quiet, and may be configured for use with any of a variety of present or future devices that indirectly supply heated air to a patient.

In various embodiments, the air treatment system may employ one or more filter to capture contaminants dispersed in the air, which may be provided as part of the existing warming blanket system. The air treatment system may include an intake area with an opening to the surrounding air, and a filter. Air that passes through the opening may be filtered by the filter, and provided to the remainder of the air treatment system for purification. A fan may create an airflow of the filtered air from the intake area to a heating assembly, which may include heating elements and a controller that regulates power supplied to the heating elements. In some embodiments, the controller may also regulate power supplied to the fan. In some embodiments, the filter, fan, and heating assembly may be components that are part of the existing warming blank system. Once heated, the airflow may pass into a sanitizing chamber that is configured with multiple UV LEDs in at least one array. In various embodiments, the UV LED arrays may be connected to control circuitry that regulates power supplied to the UV LEDs. In some embodiments, the sanitizing chamber and control circuitry may be configured to fit within a base region of the existing warming blanket system. Once the heated airflow passes through the sanitizing chamber, the sanitized airflow may be passed through an exhaust hose to a warming blanket.

In various embodiments, the sanitizing chamber may include straight regions and bends, forming a shape that is configured to prevent spurious UV radiation from escaping the sanitizing chamber while providing the airflow with sufficient UV radiation dosage to achieve a desired kill rate (e.g., at least 99%).

In various embodiments, at least one array of high-output UV-emitting LEDs may be positioned within at least one straight region of the sanitizing chamber. The UV LEDs may be selected based upon the desired wavelength and power rating. In some embodiments, the UV LEDs in the at least one array emit radiation at one or more wavelength within the range of 240-280 nm, such as within the range of 260-270 nm.

The internal surface of one or more section of the sanitizing chamber may be coated with a reflective material. In some embodiments, the internal surface of the sanitizing chamber may be configured with a band of UV radiation-absorptive material. In some embodiments, any other surface that could be exposed by line of sight to components that may be adversely affected or degrade by UV radiation (e.g., the heating assembly, fan, filter, and/or exhaust hose) may also be coated with a UV radiation-absorptive material.

Design of the air treatment system for may include minimizing noise production from the fan. Therefore, the fan included in embodiment air treatment systems may be of the smallest size and/or operate at a minimum level needed to provide an effective flow rate to mobilize latent pathogens within for treatment. For example, such effective flow rate may be within the range of 180 to 300 cubic feet per minute, such as 250 cubic feet per minute. In various embodiments, the configuration of the sanitizing chamber is critical in order to manage the UV radiation flux and effectively sanitize the heated airflow without compromising the desired airflow rate. Generally, increasing the length of the pathway, such as by increasing the number and degree of bends of an airflow pathway, leads to longer residence time for the airflow, and therefore improves effectiveness of the UV radiation in killing airborne pathogens. However, such increases lengthen to the path of the airflow also increases the pressure drop over the system. Increases in pressure drops over the systems may result in an increase in overall noise generated by the system. Thus, designs of such systems seek to mitigate such pressure drops. Also, a high level of reflectance within the sanitizing chamber generally maximizes the effectiveness of the UV LEDs. However, ensuring that such reflected radiation does not escape the sanitizing chamber is critical to avoid impacting components of the warming blanket system. As a result, the fan output required to achieve the same flow rate would be increased. Therefore, the level of noise generated by operation of an air treatment system directly depends on the fan requirements, and should be minimized for patient comfort.

These constraints may be balanced to provide a compact, low noise, air treatment device for a warming blanket that achieves a sufficient pathogen kill rate. In various embodiments, a ratio of a radius of curvature of the at least one bend to a length of a straight region of the sanitizing chamber may be configured to minimize pressure drop across the air treatment system, while enabling at least a 99% reduction of airborne pathogens from the airflow and substantially no escape of UV radiation.

In various embodiments, a ratio of the length of at least one straight region in the sanitizing chamber to its cross-sectional area may be configured to optimize UV irradiation, particularly adjacent the exhaust tube.

In various embodiments, the filter may be a HEPA filter to capture and remove fine particles from the airflow. The filter may alternatively or additionally include a pre-filter that captures large particulate materials from the intake airflow. In some embodiments, the filter may additionally or alternatively include a carbon-activated filter to remove gaseous pollutants from the airflow, for example, after passing through a pre-filter and/or HEPA filter.

In various embodiments, an electronics and control module may regulate power input into the sanitizing chamber, driving the UV LEDs. The electronics and control module may operate with conventionally available power supplies and contain a circuit breaker.

Figure 5:
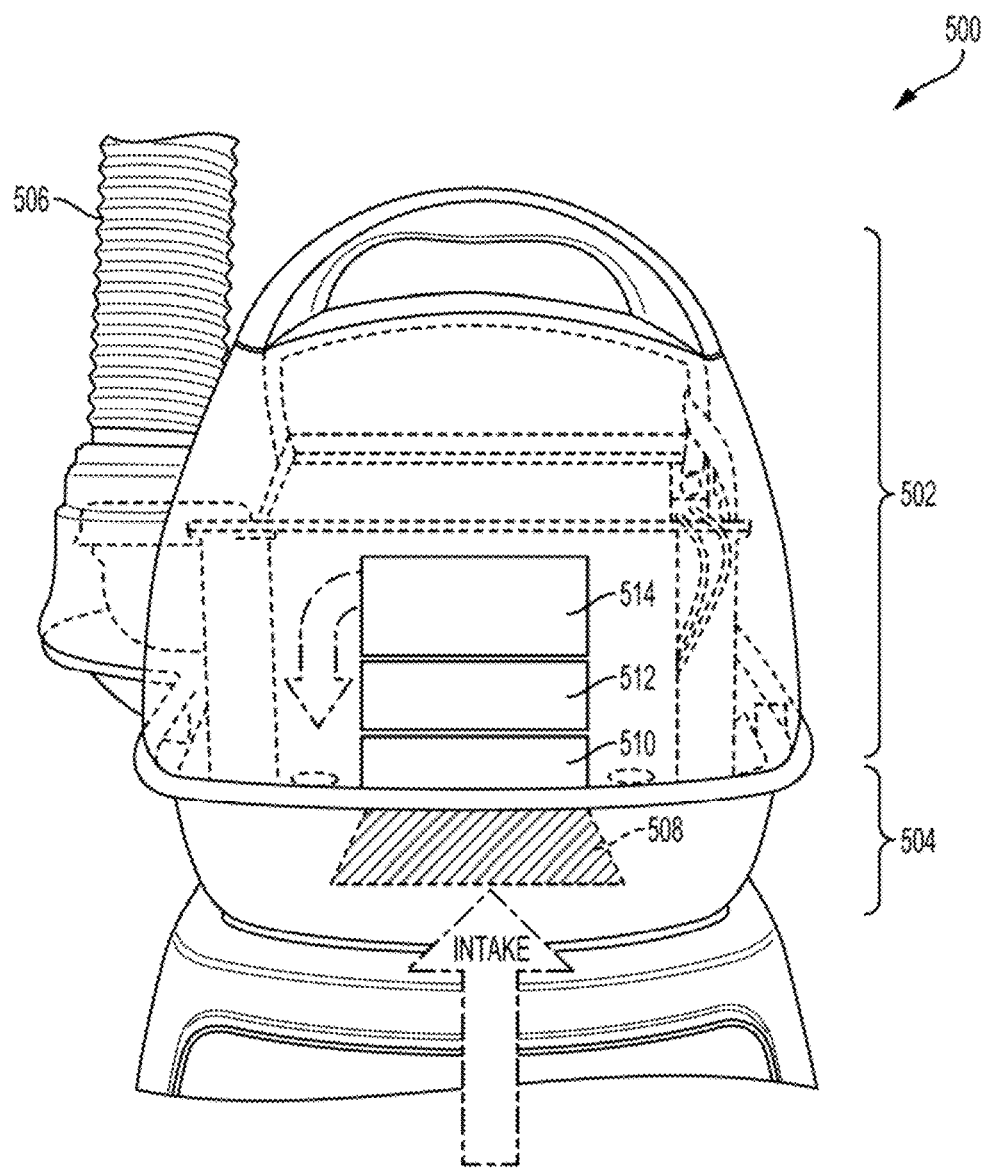
FIG. 5 is a cutaway view of an air treatment device according to various embodiments.

FIG. 5 illustrates an air treatment device 500 for a warming blanket according to various embodiments. The device 500 may include a top area 502 that is detachable from a base area 504, as well as an exhaust hose 506 to a warming blanket. The top area 502, base area 504, and exhaust hose 506 may all be provided as part of an existing warming blanket system. The underside of the base area 504 may include an intake area 508, which may include a grill covering an opening that allows air to enter the device 500. Air from the intake area 508 may be provided to a filter 510 in the top area for removing particles and contaminants in the intake air. The filtered air may feed into a fan 512 in the top area that generates airflow upwards to a heating assembly 514. The heated airflow may pass into a sanitizing chamber that is configured to fit within the base area 504 of the device 500. In various embodiments, the air treatment device 500 may include any number of additional components, all of which may be enclosed within a housing of an existing warming blanket system.

Figure 6:
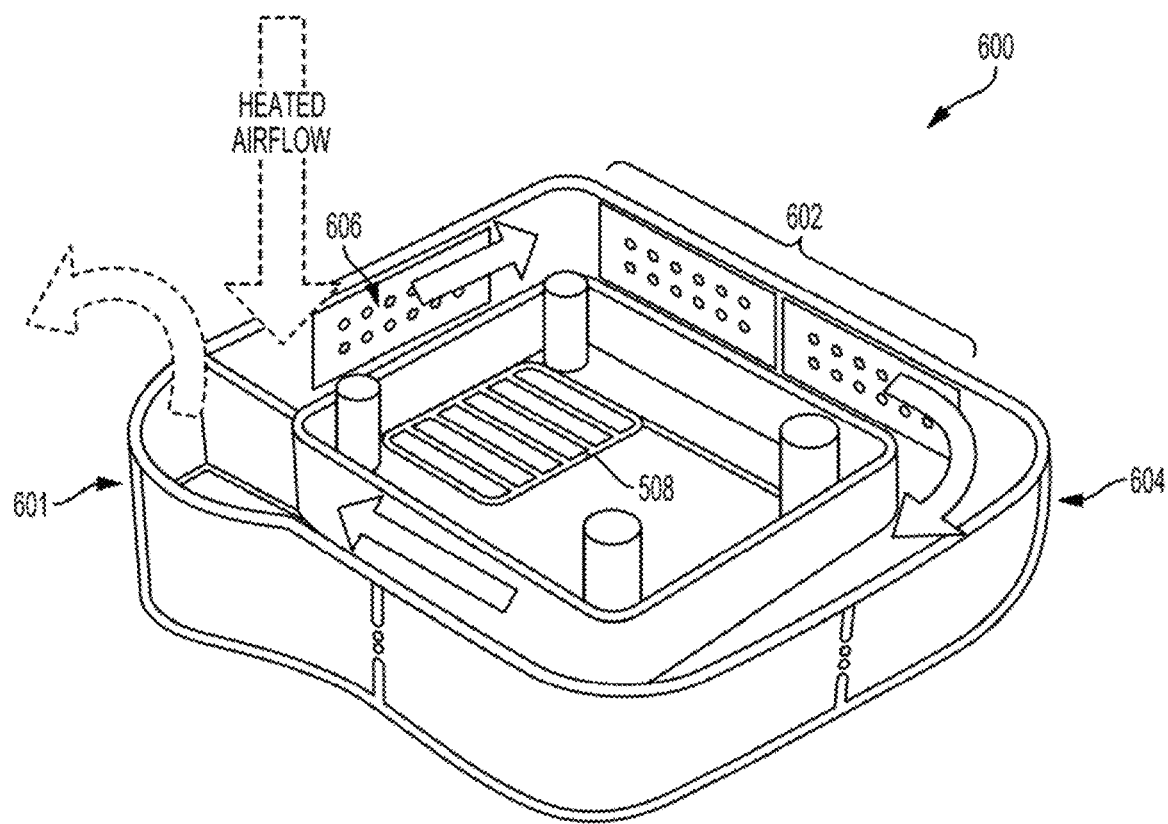
FIG. 6 is a cutaway view of a sanitizing chamber in the air treatment device of FIG. 5.

FIG. 6 illustrates a sanitizing chamber 600 that is configured for use in the air treatment device 500 of FIG. 5. With reference to FIGS. 5-6, the sanitizing chamber 600 may fit within the base area 504, around a center that includes the intake area 508 that draws air from the surrounding environment. In various embodiments, a heated airflow may enter the sanitizing chamber 600 from a heating assembly (e.g., 514), and may travel clockwise around the sanitizing chamber 600, and provide output to an area 601 that connects to an exhaust hose (e.g., 506).

In some embodiments, the sanitizing chamber 600 may have at least one straight region 602, and at least one bend 604. In some embodiments, the straight region(s) 602 may include at least one UV LED array 606. The number, curvature, and position of the bend(s) 604 in the sanitizing chamber 600 may be optimized to fit within the base area 504 while preventing escape of substantially all UV radiation, exposing the airflow to a sufficiently high UV radiation dosage, and minimizing the pressure drop in the system. The UV LEDs of the arrays may be positioned to obtain the maximum amount of UV reflectance based on the configuration of the straight region(s) 602 and the bend(s) 604, as well as to avoid escape of the UV radiation from the sanitizing chamber 600. In various embodiments, such positioning may be obtained using UV radiation ray tracing technology.

The interior surface(s) of the bends 604 and/or the straight region(s) 602 in the sanitizing chamber may be coated with a highly reflective material, such as polished aluminum. In some embodiments, the interior surface of the bends 604 and/or the straight region(s) 602 may be coated with a naturally germicidal material, such as copper or copper alloy.

In some embodiments, the airflow of the air treatment device 100 may be within the range of about 100 cubic feet per minute (cfm) to about 700 cfm. In some embodiments, the air treatment device 100 may be configured such that the pressure drop is within the operating parameters of the fan 104. For example, if the fan 104 is capable of producing an airflow of 500 cfm, the total pressure drop may be less than 0.7 inches of water. In some embodiments, the airflow within the sanitizing chamber may have one or more areas of turbulence within the sanitizing chamber, providing a high Reynolds number (e.g., Reynolds number above 20,000).

An electronics and control module may be incorporated to regulate power supplied to the UV LED array(s) 606. In some embodiments, the electronics and control module 608 may be configured to fit into the center portion of the base area 504. The electronics and control module may be provided as one or multiple units/integrated circuits, and may be coupled to a power supply for the air treatment device.

As described, while the sanitizing chamber is configured to expose the airflow to a sufficiently high UV radiation dosage, a number of parameters of the sanitizing chamber may be adjusted to optimally prevent escape of the UV radiation, while maintaining a compact size and low noise production of the device. In particular, such parameters may include those affecting the geometry of the sanitizing chamber, such as the total bend angle for the airflow in the sanitizing chamber, and the ratio of the sanitizing chamber length to its diameter. The diameter of the sanitizing chamber in various embodiments may be represented by its cross-sectional area ("L/A ratio"), which may be calculated by multiplying the width of the sanitizing chamber by its height.

In some embodiments, the total bend angle may be the result of a plurality of bends in the sanitizing chamber, for example the four bends 602 in the sanitizing chamber 600 as four bends. In other examples, the sanitizing chamber may have between two and five bends, which may be in one or multiple orientation planes. In alternative embodiments, the total bend angle may be the result of one bend, such as between two straight channels.

In various embodiments, the sanitizing chamber may have dimensions such that the L/A ratio is at least 25, and may be configured with a total bend angle of at least 90 degrees (e.g., 360 degrees in the sanitizing chamber 600). Within these ranges, such parameters may be adjusted to comport with the specific features, measurements, and other properties of the device, as well as minimize size and pressure drop (i.e., noise).

Figure 7:
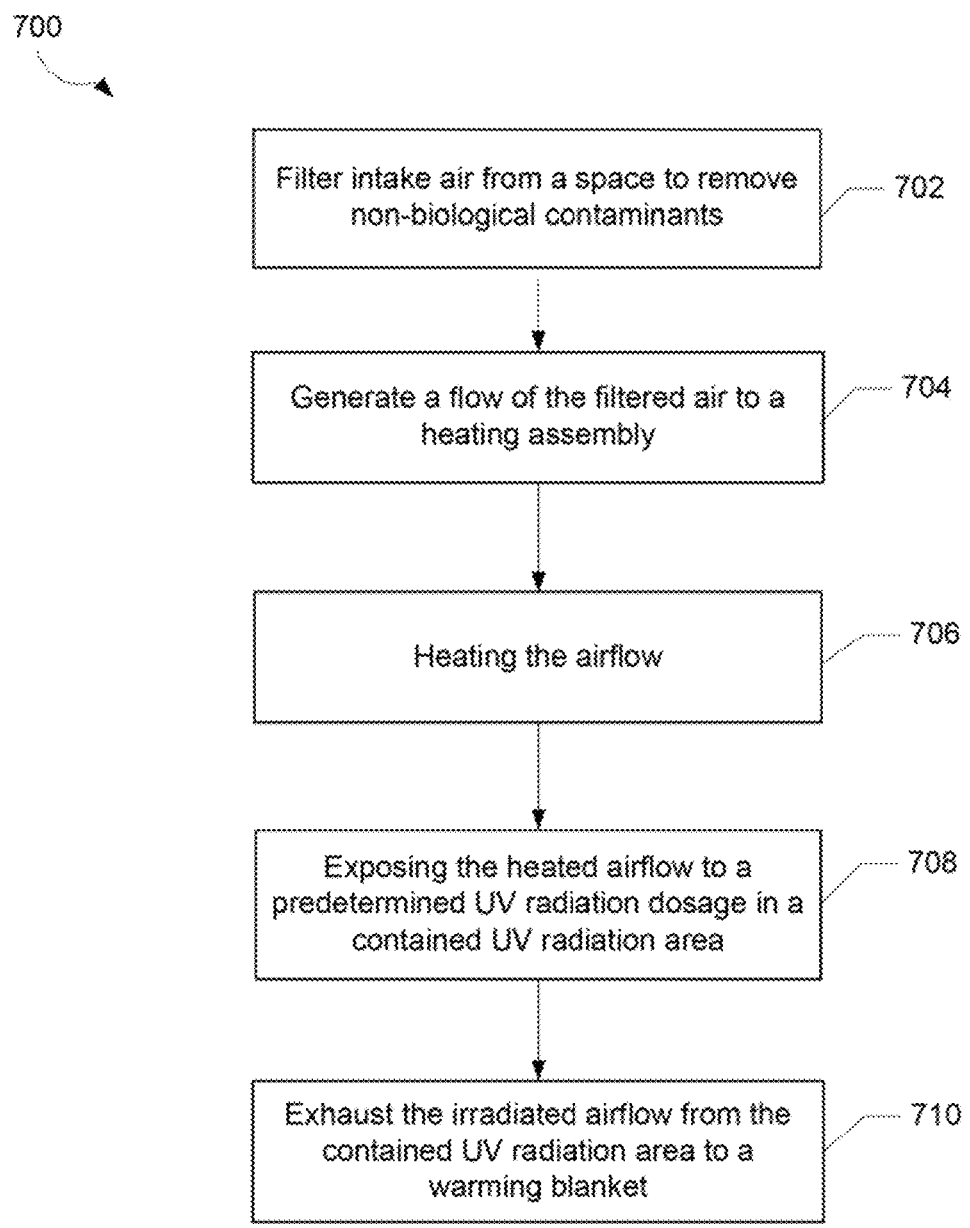
FIG. 7 is a process flow diagram illustrating a method for reducing airborne contaminants in an airflow for a warming blanket according to various embodiments.

FIG. 7 shows an embodiment method 700 for purifying air that is provided to a warming blanket for a patient. In block 702, intake air from a space may be filtered to remove non-biological contaminants.

In various embodiments, such filtering may involve using at least one filter that removes fine particulates (e.g., HEPA filter) and/or that adsorbs harmful gasses (e.g., volatile organic chemical filter). In block 704, an airflow may be generated to push the filtered air to a heating assembly. In various embodiments, the airflow may be generated by a fan, and the heating assembly may include heating elements and a controller.

In block 706, the airflow may be heated by the heating assembly. In block 708, the heated airflow may be exposed to a predetermined UV radiation dosage in a contained UV radiation area. In various embodiments, the contained UV radiation area may be a chamber with an array of UV LEDs (e.g., the sanitizing chamber 600 in FIG. 6). In various embodiments, the shape and size of the contained UV radiation area, and the position of the UV LEDs, may be configured to prevent spurious UV radiation outside of the contained area.

The predetermined UV radiation dosage may be achieved by optimizing the number and position of the UV LEDs and the materials used within the contained UV radiation area, and configuring the contained UV radiation area to allow for a necessary residence time. In various embodiments, the predetermined UV radiation dosage for a hospital setting may be sufficient to kill or disable at least 99% of airborne pathogens within the airflow.

In block 710, the irradiated airflow may be exhausted from the contained UV radiation area to a warming blanket. In some embodiments, the irradiated airflow may pass from the contained UV radiation area to an exhaust hose that is coupled to the warming blanket.

In some embodiments, additional functionality may be added to an air treatment system by including specialized components. For example, a UV sensor may be disposed within the sanitization chamber of embodiment air treatment devices in order to monitor the radiation flux and ensure proper operation. In various embodiments, such UV sensor may use one or more UV photodetector, such as those based on gallium nitride (GaN), indium gallium nitride (InGaN), and/or aluminum gallium nitride (AlGaN) materials. In various embodiments, the UV sensor may be configured to communicate with an externally visible indicator to confirm to the user that the device is working. In some embodiments, the indicator may be included as part of an air treatment device, whereas in other embodiments the indicator may be provided by a separate device in wireless communication with the air treatment device.

Figure 8:
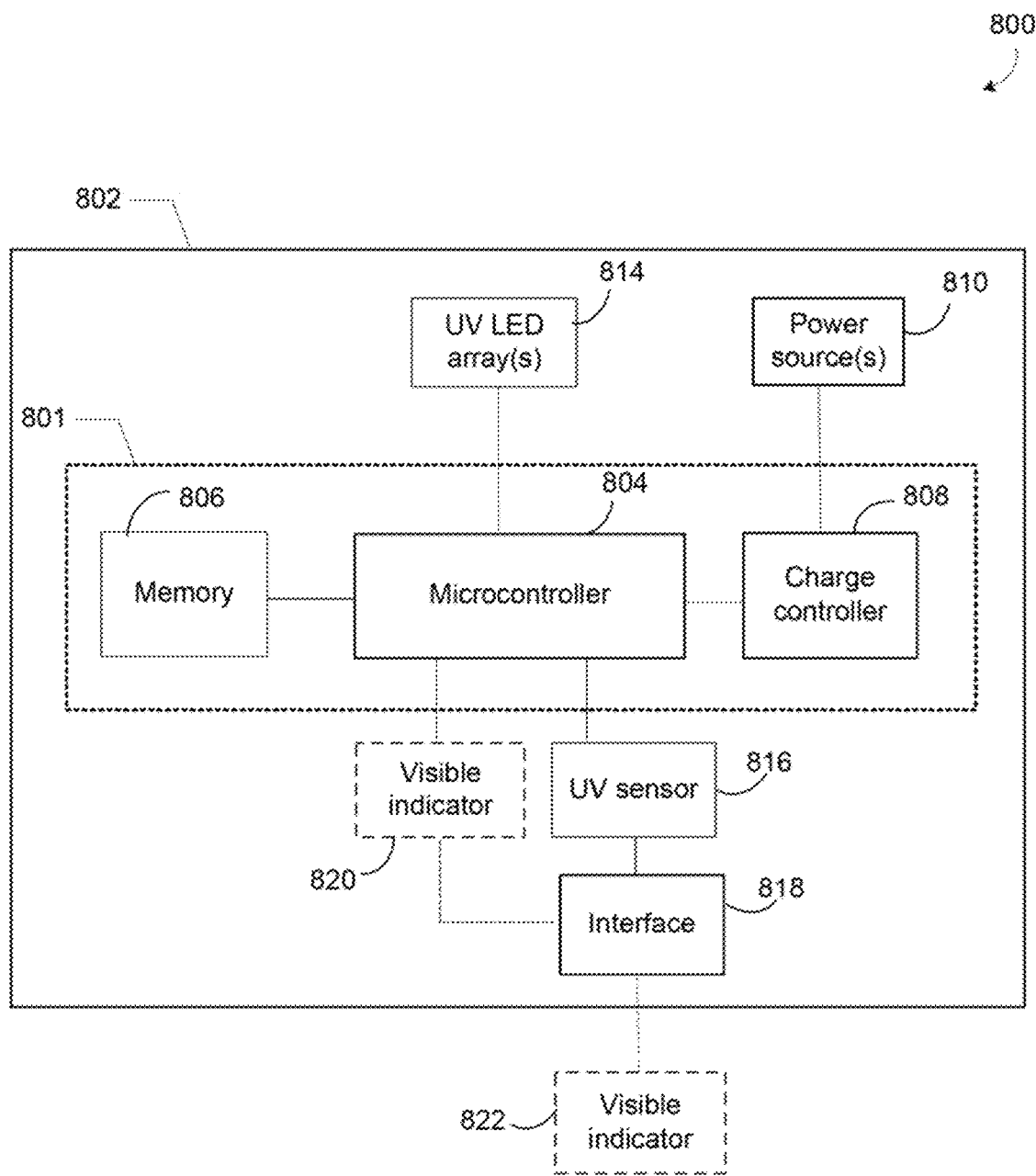
FIG. 8 is a component block diagram of an air treatment system according to various embodiments.

FIG. 8 illustrates components of an example air treatment system 800. In system 800, an electronics and control module 801 may be implemented on a circuit board within an air treatment device 802. With reference to FIGS. 5-8, the circuit board may be incorporated into the base area 504 of the air treatment system 500, and may be separate from one or more controller for the heating elements and/or fan. The electronics and control module 802 may include a microcontroller 804 coupled to a memory device 806 and a charge controller 808. The charge controller 808 may connect to at least one power source 810, which may be an AC power supply and/or a battery. Other components within the air treatment system 800 may include one or more UV LED array 814, and a UV sensor 816. The UV sensor 816 may be connected to an interface 818 that connects one or more visible indicator. An optional visible indicator 820 may be provided as part of the air treatment device 802. The visible indicator 820 may be coupled to the microcontroller 804 and the interface 818. Another optional visible indicator 822 may be provided as an external component, which may be part of another device or system (e.g., a smartphone, tablet, etc.). The interface 818 may connect the visible indicator 822 through a wireless communication link.

The UV LEDs of the one or more array may be electrically connected to the electronics and control module and fixedly attached to mated openings in the walls of a portion of the sanitizing chamber (e.g., straight region) such that the UV LED array circuit boards are outside of the sanitizing chamber and the UV LEDs irradiate inside the sterilization region of the sanitizing chamber. The UV sensor may be electrically connected to the electronics and control module and fixedly attached to a mated opening in the wall of the sanitizing chamber such that the sensor can detect irradiance levels.

EXAMPLES

The effects of two different variations in the sanitizing chamber were tested for efficacy in preventing UV radiation escape. The sanitizing chamber that was used had an overall length of 36 inches, and was equipped with four Nikkiso VPS131 producing 10 mW of radiation at 265 nm.

A coating of Alanod MIRO2 (4200GP) was applied to create the reflective surface within the reflective portion of the sanitizing chamber, resulting in a reflectivity of 95%, The surface within the diffuser portion of the sanitizing chamber was hard coat anodized, resulting in an absorptivity of 90%. Results were assessed in the context of the exposure limit to UV radiation based on a maximum daily exposure of 30 J/m$^2$, set forth in "A Non-Binding Guide to the Artificial Optical Radiation Directive 2006/25/EC, by the European Agency for Safety and Health at Work. Specifically, the exposure limit for a duration of 8 hours is provided at 1 mW/m$^2$.

Ray tracing analysis was used to provide the average power of UV radiation leakage at the exhaust end of the sanitizing chamber.

Example 1: Angle of Bend in Sanitizing Chamber

Sanitizing chambers were created with two 18 inch sections connected by a single bend, which has an angle of either 90 degrees or 180 degrees. A comparative sanitizing chamber having a bend angle of 0 degrees (i.e., no bend) was also created. The sanitizing chambers each had a fixed cross-sectional area of 18.06 in$^2$ (i.e., 4.25 inches wide by 4.25 inches high). The average irradiance leakage from the sanitizing chambers having these bend angles was measured, with the following results:

| Bend Angle | Average UV radiation leakage (mW/m$^2$) | Percentage of maximum leakage | Percent reduction from maximum average |
|---|---|---|---|
| 0° | 4.69 | 100.00% | 0% |
| 90° | 0.288 | 6.14% | −93.86% |
| 180° | 0.125 | 2.67% | −97.33% |

The results above indicate that the use of a straight (i.e., 0° of bend) sanitizing chamber with a 2.0 L/A ratio does not attenuate the irradiance leakage, resulting in an average UV radiation leakage that is above the 1 mW/m$^2$ Artificial Optical Radiation Directive 8 hour exposure limit.

The results above indicate that the bend angles of 90 degrees and 180 degrees reduce the UV radiation leakage by 93.86% and 97.33% respectively, over the 0 degrees/maximum leakage baseline, and provide average irradiation measurements that are well under the 1 mW/m$^2$ limit.

Figure 9A:
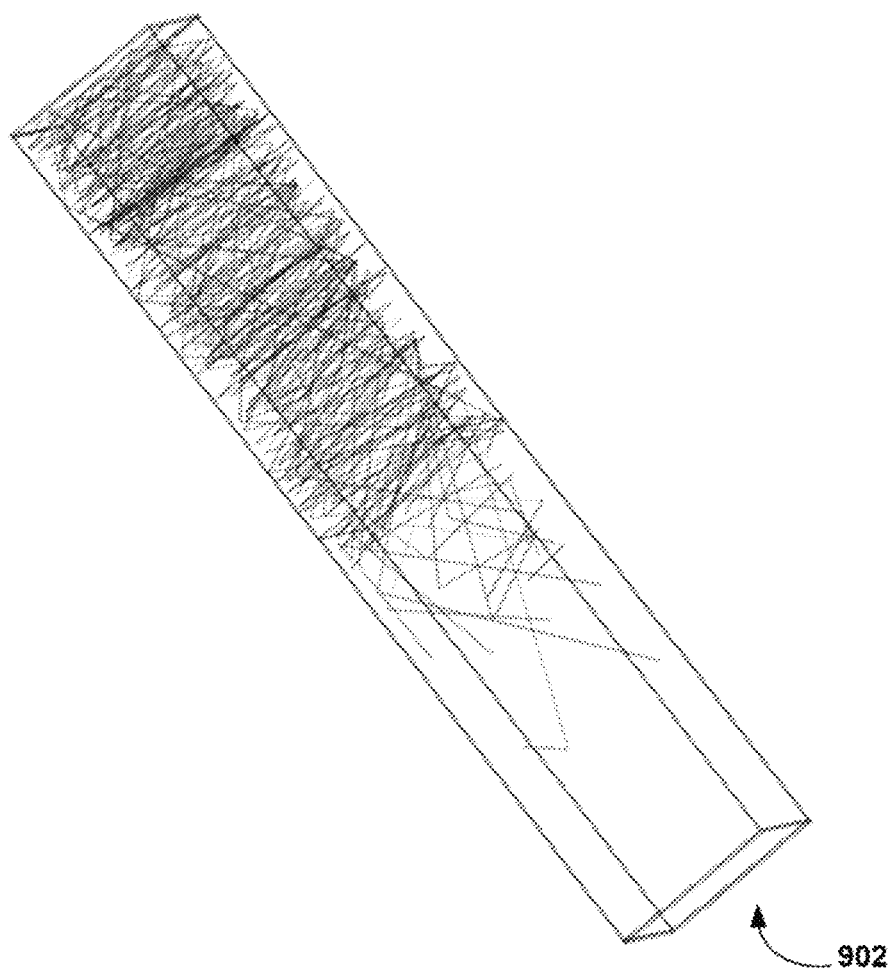
FIGS. 9A-9C are computer-generated three-dimensional representations of the reflectance of UV radiation within sanitizing chambers having various bend angles.
Figure 9B:
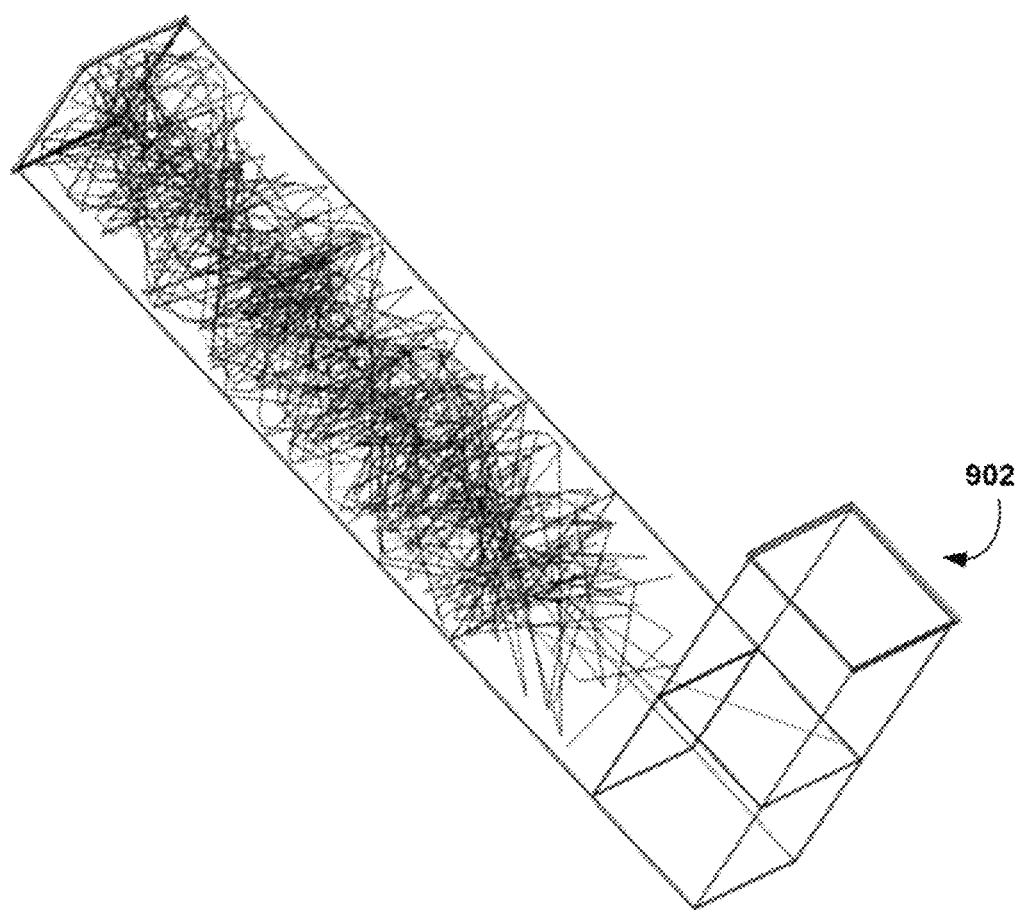
Figure 9C:
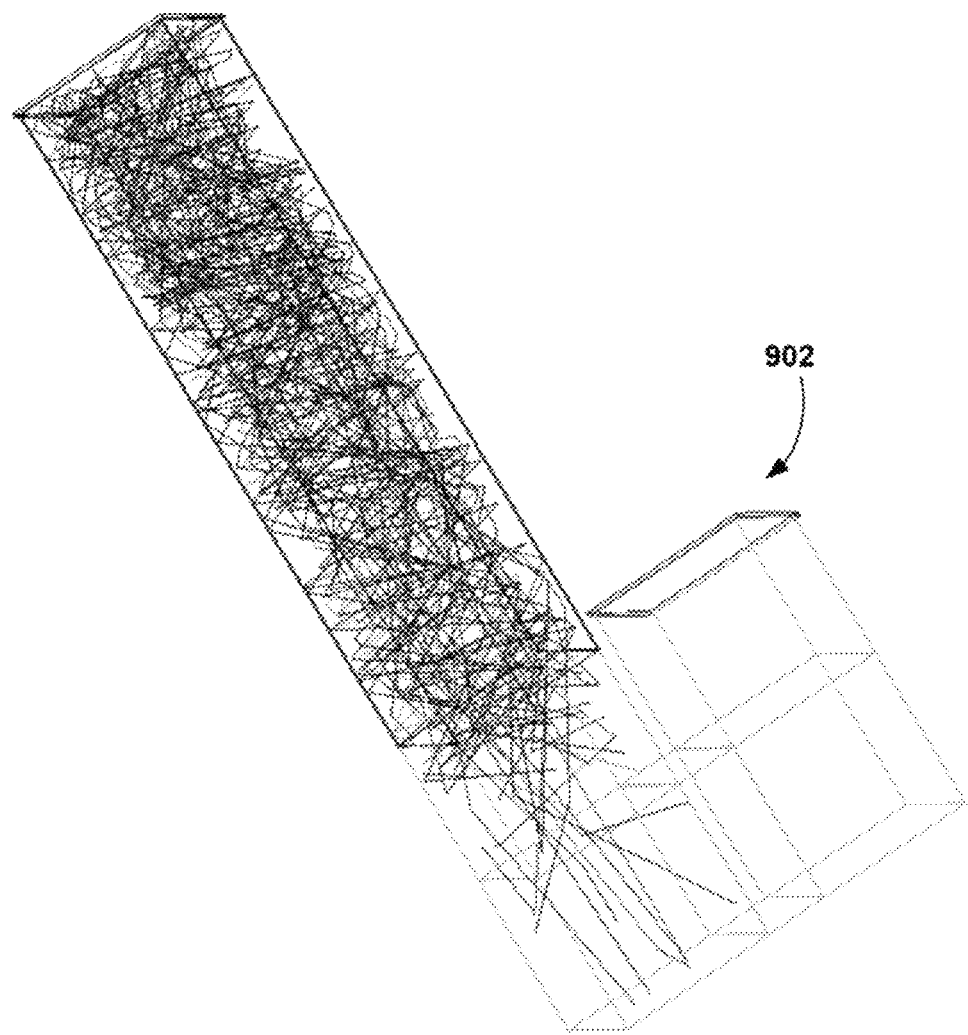
Figure 9F:
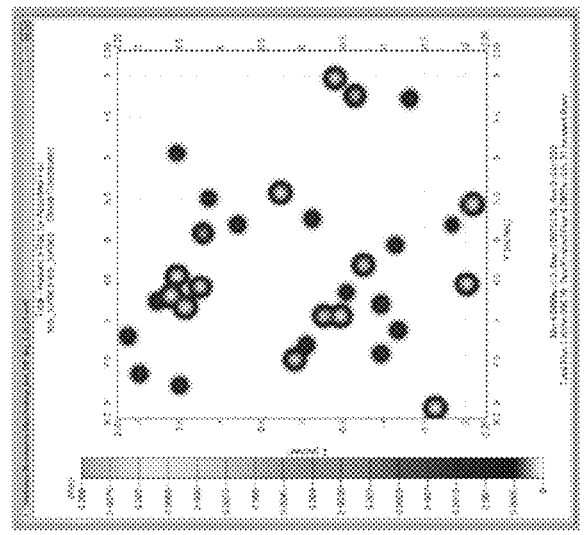
FIGS. 9D-9F are computer-generated irradiation maps showing the amount of incident UV radiation escape from the sanitizing chambers represented in FIGS. 9A-9C, respectively.
Figure 9E:
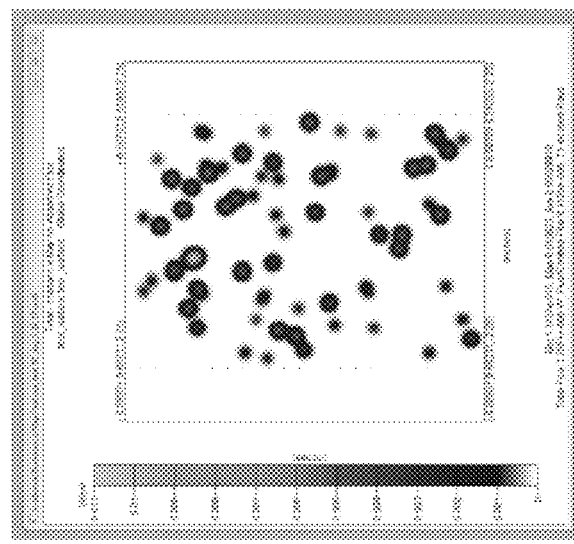
Figure 9D:
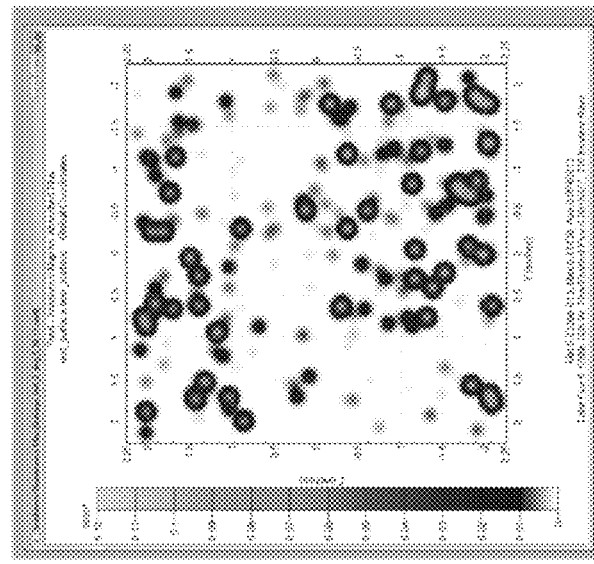

Computer-generated models tracing the reflectance of UV radiation rays in three-dimensional space within each of the tested sanitizing chambers (i.e., with 0°, 90°, and 180° of bend) are shown in FIGS. 9A-9C, respectively. FIGS. 9D-9F are irradiation maps that show the amount of incident UV radiation escaping the respective sanitizing chambers modeled in FIGS. 9A-9C. Specifically, the irradiation maps in FIGS. 9D-9F each provide the computer-modeled density of UV radiation rays measured at a cross-section near the exit end 902 of the particular sanitizing chamber.

A visual comparison of FIGS. 9D-9F demonstrates that the lowest level of UV radiation escape occurs in FIG. 9F, which corresponds to the model of the sanitizing chamber having 180° of bend, shown in FIG. 9C.

Example 2: Length to Cross-Sectional Area Ratio of Sanitizing Chamber

Ten sanitizing chambers having a length of 36 inches were created with varying width and height dimensions, listed below:

| No. | Width (in) | Height (in) | Cross-sectional area (in$^2$) |
|---|---|---|---|
| 1 | 1.00 | 1.00 | 1.00 |
| 2 | 1.20 | 1.20 | 1.44 |
| 3 | 1.50 | 1.50 | 2.25 |
| 4 | 2.19 | 2.19 | 4.80 |
| 5 | 2.68 | 2.68 | 7.20 |
| 6 | 3.00 | 3.00 | 9.00 |
| 7 | 3.21 | 3.21 | 10.29 |
| 8 | 4.25 | 4.24 | 18.02 |
| 9 | 6.375 | 6.375 | 40.64 |
| 10 | 8.5 | 8.5 | 72.25 |

Based on their dimensions, the L/A ratios of the sanitizing chambers 1-10 ranged from 0.5 to 36. The sanitizing chambers each had a fixed bend angle of 0 degrees (i.e., no bend). The average irradiance leakage from each of sanitizing chambers 1-10 was measured, for which results are provided below with the corresponding L/A ratio:

| No. | L/A ratio | Average UV radiation leakage (mW/m$^2$) | Cross-sectional area (in$^2$) |
|---|---|---|---|
| 1 | 36.00 | 0.721 | 1.00 |
| 2 | 25.00 | 0.941 | 1.44 |
| 3 | 16.00 | 1.45 | 2.25 |
| 4 | 7.50 | 2.17 | 4.80 |
| 5 | 5.00 | 3.02 | 7.20 |
| 6 | 4.00 | 3.27 | 9.00 |
| 7 | 3.50 | 3.58 | 10.29 |
| 8 | 2.00 | 4.69 | 18.02 |
| 9 | 0.89 | 7.78 | 40.64 |
| 10 | 0.50 | 8.68 | 72.25 |

The data reveal that L/A ratios of 25 and greater reduce the UV radiation leakage to an amount that is below the 1 mW/m$^2$ exposure limit.

For example, computer-generated models tracing reflectance of UV radiation rays in three-dimensional space within the tested sanitizing chamber no. 2 (i.e., with L/A ratio of 25), no. 4 (i.e., with L/A ratio of 7.5), no. 6 (i.e., with L/A ratio of 4), and no. 9 (i.e., with L/A ratio of 0.89) are respectively shown in FIGS. 10A-10D. FIGS. 10E and 10F are irradiation maps that respectively show the amount of incident UV radiation escaping the sanitizing chambers modeled in FIGS. 10A and 10D. Specifically, the irradiation maps in FIGS. 10E and 10F provide the computer-modeled density of UV radiation rays measured at a cross-section near the exit end 1002 of the particular sanitizing chamber.

Figure 10B:
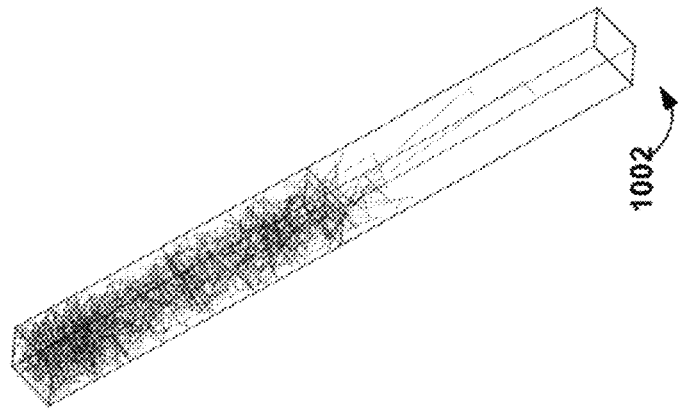
FIGS. 10A-10D are computer-generated three-dimensional representations of the reflectance of UV radiation within sanitizing chambers having various length-to-area ratios.
Figure 10A:
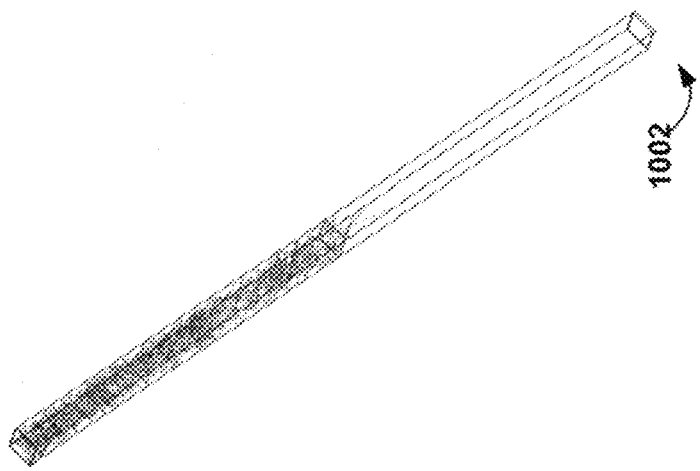
Figure 10C:
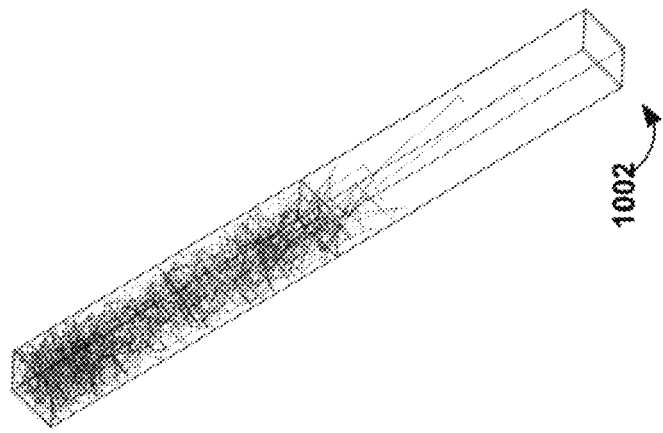
Figure 10D:
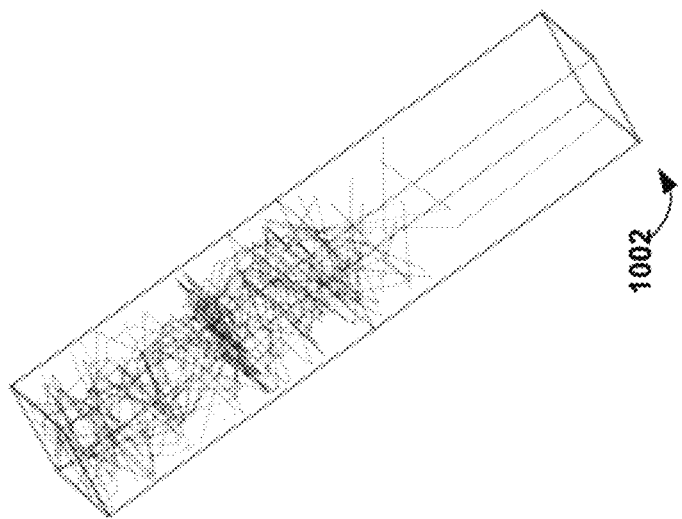
Figure 10F:
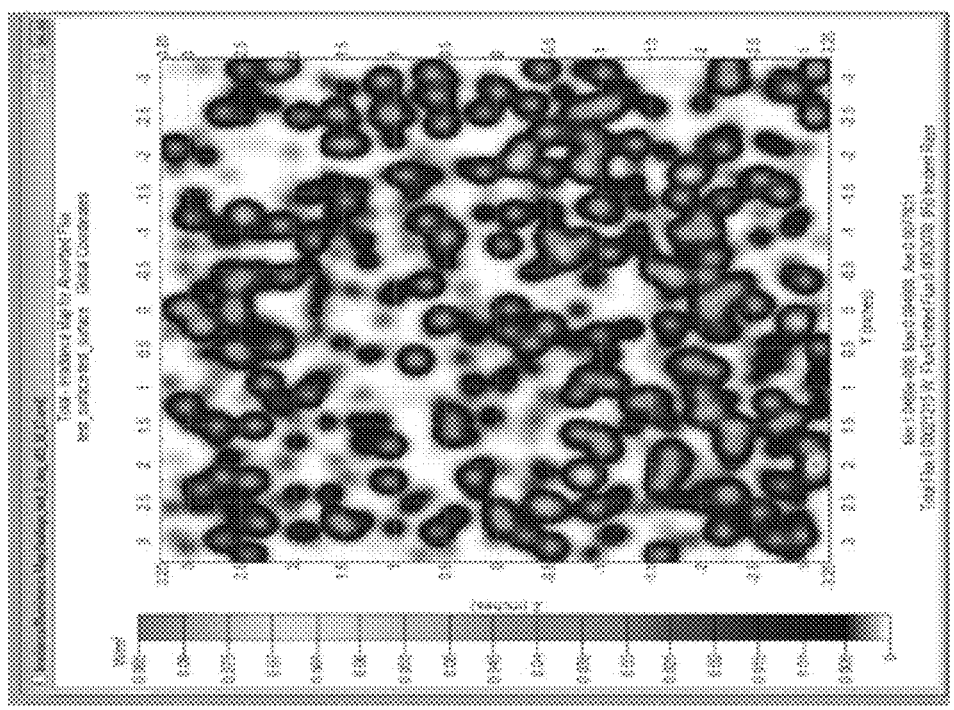
FIGS. 10E and 10F are computer-generated irradiation maps showing the amount of incident UV radiation escape from the sanitizing chambers represented in FIGS. 7A and 7B, respectively.
Figure 10E:
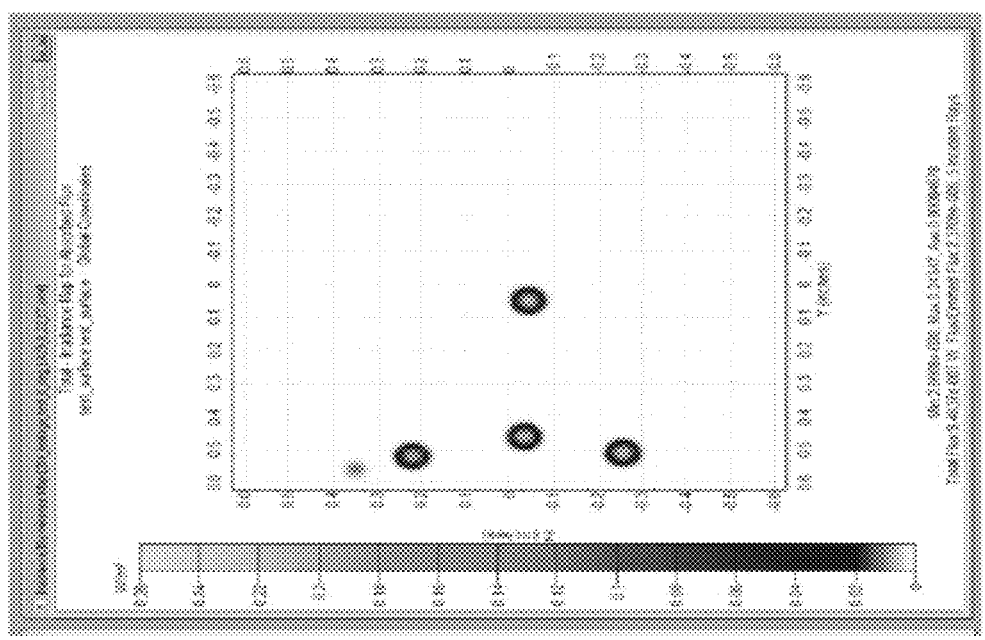

A visual comparison of FIGS. 10E and 10F demonstrates a far lower level of UV radiation escape occurring in FIG. 10E, which corresponds to the model of the sanitizing chamber having the L/A ratio of 25 (i.e., tested sanitizing chamber no. 2) shown in FIG. 10A.

Figure 11:
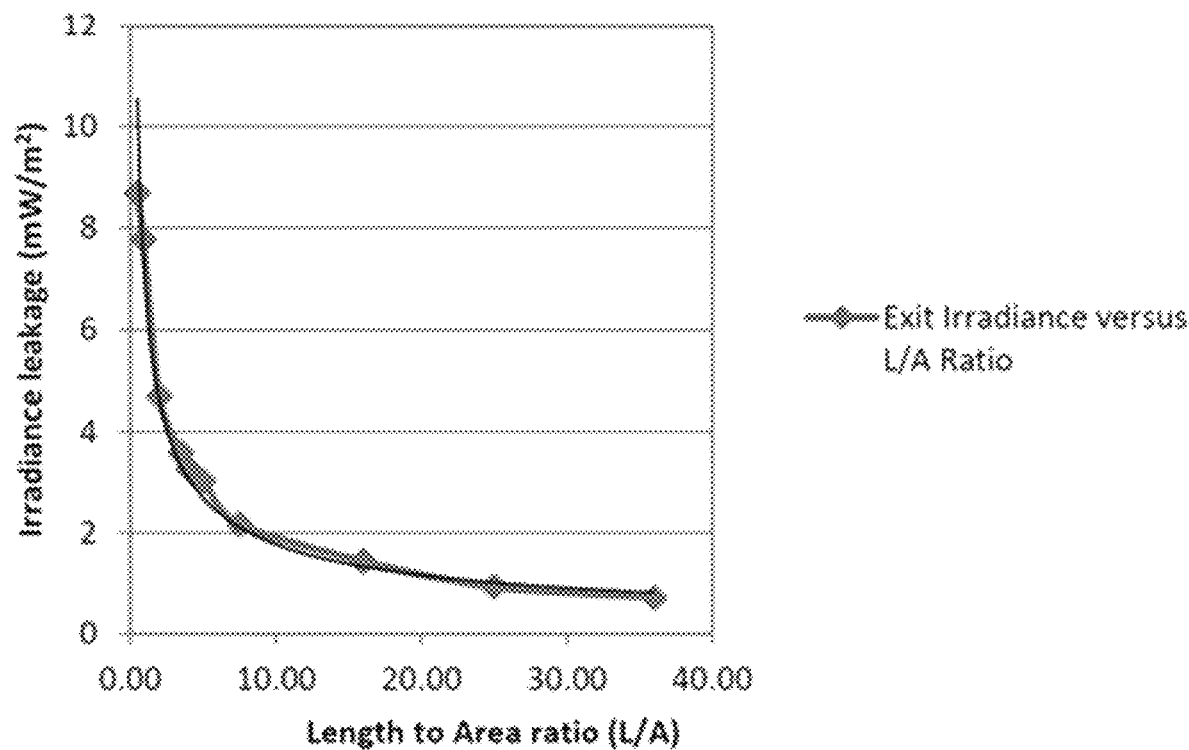
FIG. 11 is a graph illustrating the average UV radiation leakage measured as a function of the ratio of length to cross-sectional area for example sanitizing chambers.

FIG. 11 shows the average UV irradiance escape for each of the sanitizing chambers 1-10 of Example 2. The data in the graph of FIG. 11 show a trend in which an increase in the L/A ratio reduces the average level of UV irradiance escape measurement. Using an automatic curve fitting analysis, the following mathematical function was generated to represent the data points:

$$\text{Average UV radiation leakage} = 6.9656(L/A \text{ ratio})^{-0.594} \quad \text{(Equation 1)}.$$

Together, the effective configurations for the sanitizing chamber that are shown above (i.e., bend angle of at least 90 degrees, and an L/A ratio of at least 25) may be implemented in combination and adjusted to identify optimal configurations for the particular sanitizing chamber properties (e.g., length of sanitizing chamber, number of bends, etc.).

In light of the foregoing description, it should be recognized that embodiments in accordance with the present invention can be realized in numerous configurations contemplated to be within the scope and spirit of the claims. Additionally, the description above is intended by way of example only and is not intended to limit the present invention in any way, except as set forth in the following claims.

What is claimed is:

1. An air treatment system comprising:
   an air intake area comprising an opening and a filter assembly;
   a fan configured to generate an airflow of filtered air;
   a heating assembly configured to heat the airflow;
   a sanitizing chamber configured to expose the heated airflow to ultraviolet (UV) radiation, wherein the sanitizing chamber comprises:
      at least one bend having a total bend angle of at least 90 degrees; and
      at least one straight region, wherein the at least one straight region includes a sterilization region comprising an array of ultraviolet (UV) light emitting diodes (LEDs), wherein a ratio of a total length of the sanitizing chamber to a cross-sectional area of the sanitizing chamber is at least 25; and
   an exhaust portion coupled to a warming blanket, wherein the exhaust portion is configured to receive the heated airflow that has passed through the sanitizing chamber.

2. The air treatment system of claim 1, wherein the at least one bend comprises a plurality of bends.

3. The air treatment system of claim 1, wherein the at least one bend has a total bend angle of 360 degrees.

4. The air treatment system of claim 1, wherein a length of the sterilization region is configured to minimize pressure drop across the air treatment system while enabling a 99% reduction of airborne pathogens from the airflow.

5. The air treatment system of claim 1, wherein a length of the sterilization region and the total bend angle are configured to fit within a base portion of a warming blanket system.

6. The air treatment system of claim 1, wherein the number of bends, the total bend angle, and the ratio of the total length of the sanitizing chamber to the cross-sectional area are configured to minimize pressure drop across the air treatment system while preventing escape of at least 99% of the UV radiation from the sanitizing chamber.

7. The air treatment system of claim 1, wherein the filter assembly comprises a high-efficiency particulate air (HEPA) filter.

8. The air treatment system of claim 1, wherein the array of UV LEDs is configured to emit radiation at one or more wavelength within a range of 240-280 nm.

9. The air treatment system of claim 1, wherein the UV LEDs are configured to irradiate the airflow with a UV radiation dosage, wherein the UV radiation dosage is calculated based on a computed residence time for the sanitizing chamber, computed UV radiation flux, and desired threshold of 99% reduction in airborne pathogens.

10. The air treatment system of claim 1, wherein a UV-reflective material covers at least some of an interior surface of the sanitizing chamber.

11. The air treatment system of claim 1, further comprising a UV sensor disposed in the sanitizing chamber, and at least one visible indicator, wherein the UV sensor monitors performance of the array of UV LEDs, and the at least one visible indicator provides information to a user about the performance of the array of UV LEDs.

12. A method of reducing airborne contaminants in an airflow for a warming blanket, the method comprising:
   filtering an airflow from a room to remove non-biological contaminants;
   generating an airflow that pushes filtered air to a heating assembly configured to heat the filtered airflow;
   providing the heated airflow to a contained ultraviolet (UV) radiation area, wherein the contained UV radiation area comprises at least one bend having a total bend angle of at least 90 degrees, and wherein a ratio of a total length of the contained UV radiation area to a cross-sectional area of the contained UV radiation area is at least 25;
   exposing the airflow in the contained UV radiation area to a predetermined UV radiation dosage; and
   exhausting the irradiated airflow from the contained UV radiation area to the warming blanket.

* * * * *